United States Patent
Allen et al.

(10) Patent No.: US 6,686,163 B2
(45) Date of Patent: Feb. 3, 2004

(54) CODING SEQUENCE HAPLOTYPE OF THE HUMAN BRCA1 GENE

(75) Inventors: Antonette C. P. Allen, Severn, MD (US); Tracy S. Angelly, Gaithersburg, MD (US); Tammy Lawrence, Laurel, MD (US); Sheri J. Olson, Falls Church, VA (US); Mark B. Rabin, Rockville, MD (US)

(73) Assignee: Gene Logic Inc., Gaithersburg, MD (US)

( * ) Notice: Subject to any disclaimer, the term of this patent is extended or adjusted under 35 U.S.C. 154(b) by 0 days.

(21) Appl. No.: 10/022,819

(22) Filed: Dec. 20, 2001

(65) Prior Publication Data

US 2003/0027166 A1 Feb. 6, 2003

Related U.S. Application Data

(62) Division of application No. 09/074,452, filed on May 6, 1998, now abandoned.

(51) Int. Cl.⁷ ............................. C12Q 1/68; C07H 21/04
(52) U.S. Cl. ....................... 435/6; 435/320.1; 435/69.1; 435/325; 536/23.1; 536/24.3; 536/24.32; 536/23.5; 530/350
(58) Field of Search ............................ 536/23.1, 24.3, 536/23.2, 23.5; 435/320.1, 6, 325, 69.1; 514/44; 530/350, 300

(56) References Cited

U.S. PATENT DOCUMENTS

| | | | |
|---|---|---|---|
| 4,458,066 A | 7/1984 | Caruthers et al. | ............... 536/27 |
| 4,683,202 A | 7/1987 | Mullis | ........................ 435/91 |
| 4,704,362 A | 11/1987 | Itakura et al. | ............... 435/253 |
| 5,221,619 A | 6/1993 | Itakura et al. | ............... 435/69.4 |
| 5,445,934 A | 8/1995 | Fodor et al. | ..................... 435/6 |
| 5,510,270 A | 4/1996 | Fodor et al. | ................. 436/518 |
| 5,545,531 A | 8/1996 | Rava et al. | ..................... 435/6 |
| 5,547,839 A | 8/1996 | Dower et al. | ..................... 435/6 |
| 5,561,058 A | 10/1996 | Gelfand et al. | ............. 435/912 |
| 5,582,989 A | 12/1996 | Caskey et al. | ................. 435/6 |
| 5,583,013 A | 12/1996 | Itakura et al. | ............... 435/69.4 |
| 5,589,330 A | 12/1996 | Shuber | ........................ 435/6 |
| 5,593,840 A | 1/1997 | Bhatnagar et al. | ............. 435/6 |
| 5,624,803 A | 4/1997 | Noonberg et al. | ............. 435/6 |
| 5,633,134 A | 5/1997 | Shuber | ........................ 435/6 |
| 5,650,316 A | 7/1997 | Aggarwal et al. | .......... 435/375 |
| 5,654,155 A | * 8/1997 | Murphy et al. | ................. 435/6 |
| 5,693,473 A | 12/1997 | Shattuck-Eidens et al. | ..... 435/6 |
| 5,709,999 A | 1/1998 | Shattuck-Eidens et al. | ..... 435/6 |
| 5,710,001 A | 1/1998 | Skolnich et al. | ................. 435/6 |
| 5,726,019 A | 3/1998 | Sidransky | ....................... 435/6 |
| 5,747,282 A | 5/1998 | Skolnick et al. | ........... 435/69.1 |
| 5,750,400 A | * 5/1998 | Murphy et al. | ................. 435/6 |
| 5,753,441 A | 5/1998 | Skolnick et al. | ................. 435/6 |
| 5,756,294 A | 5/1998 | White et al. | ..................... 435/6 |
| 5,858,669 A | 1/1999 | Levine | ......................... 435/6 |
| 5,891,857 A | 4/1999 | Holt et al. | ..................... 514/44 |
| 5,912,127 A | 6/1999 | Narod et al. | ..................... 435/6 |
| 5,948,643 A | 9/1999 | Rubinfeld et al. | .......... 435/69.1 |
| 5,965,377 A | 10/1999 | Adams et al. | .............. 435/7.23 |
| 6,033,857 A | 3/2000 | Tavtigian et al. | ............... 435/6 |
| 6,045,997 A | 4/2000 | Futreal et al. | ................. 435/6 |
| 6,051,379 A | 4/2000 | Lescallett et al. | .............. 435/6 |
| 6,083,698 A | 7/2000 | Olson et al. | ..................... 435/6 |
| 6,124,104 A | 9/2000 | Tavtigian et al. | ............ 435/7.2 |
| 6,130,322 A | * 10/2000 | Murphy et al. | ................. 435/6 |

FOREIGN PATENT DOCUMENTS

| | | |
|---|---|---|
| EP | 0705902 A1 | 4/1996 |
| EP | 0705903 A1 | 4/1996 |
| EP | 0699754 A1 | 6/1996 |
| GB | 2307477 A | 5/1997 |
| WO | WO9304200 | 3/1993 |
| WO | WO9519369 | 7/1995 |
| WO | WO9722689 | 6/1997 |
| WO | WO9730108 | 8/1997 |
| WO | WO9815654 | 4/1998 |

OTHER PUBLICATIONS

Abeliovich et al. (1997) The Founder Mutations 185deAG and 5382insCin BRCA and 6174delT in BRACA2 Appear in 60% of Ovarian Cancer and 30% of Early–Onset Breast Cancer Patients among Ashkenazi Women. *Am. J. Hum. Genetics* 60(3): 505–514.

Couch et al. (1996) Mutations and Polymorphisms in the Familial Early–Onset Breast Cancer (BRCA1) Gene. *Human Mutation* 8(1):8–18.

Dunning et al. (1997) Common BRCA1 variants and susceptibility to breast and ovarian cancer in the general population. *Human Molecular Genetics* 6(2):285–289.

Durrocher et al. (1996) Comparison of BRCA1 polymorphisms, rare sequence variants and/or missense mutations in unaffected and breast/ovarian cancer populations. *Human Molecular Genetics* 5(6): 835–842.

Friedman et al. (1994) Confirmation of BRCA1 by analysis of germline mutations linked to breast and ovarian cancer in ten families. *Nature Genetics* 8(4):399–404.

Funari et al. (1997) Growth suppression of glioma cells by PTEN requires functional phosphatase catalytic domain. *Processings of the National Academy of Sciences (USA)* 94(23): 12479–12484.

(List continued on next page.)

*Primary Examiner*—Kenneth R. Horlick
*Assistant Examiner*—Cynthia Wilder
(74) *Attorney, Agent, or Firm*—Morgan Lewis & Bockius LLP

(57) ABSTRACT

The invention is directed to isolated coding sequences and to the protein sequences they code for. The coding sequence for BRCA1(omi4) gene is provided together with the protein sequence it codes for. The BRCA1(omi4) sequence is used for identifying an individual having an increased genetic susceptibility to breast or ovarian cancer because the patient has an inherited causative mutation in their BRCA1 gene. This invention is also related to a method of performing gene therapy with the isolated BRCA1(omi4) coding sequence and protein replacement therapy with the BRCA1(omi4) protein.

25 Claims, No Drawings

OTHER PUBLICATIONS

Hacia et al. (1996) Detection of heterozygous mutations in BRCA1 using high density oligonucleotide arrays and two-colour fluorescence analysis. *Nature Genetics* 14(4):441–447.

Hogervorst et al. (1995) Rapid detection of BRCA1 mutations by the protein truncation test. *Nature Genetics* 10(2): 208–212.

Sharan et al. Murine BRCA1:Sequence and significance for Human Missense Mutations. *Human Molecular Genetics* 4(12):2275–2278.

Struewing et al. (1995) The Carrier Frequency of the BRCA1 185delAG Mutation is Approximately 1 Percent in Ashkenazi Jewish Individuals. *Nature Genetics* 11(2):198–200.

Tashiro et al. (1997) Mutations in PTEN Are Frequent in Endometrial Carcinoma But Rare in Other Common Gynecological Malignancies[1]. *Cancer Research* 57(18): 3935–3940.

Vile et al. (1994) Gene Transfer Technologies for the Gene Therapy of Cancer. *GeneTherapy* 1(2): 88–98.

Arteaga, C. and Holt, J., "Tissue–targeted Antisense c–fos Retroviral Vector Inhibits Established Breast Cancer Xenograts in Nude Mice," *Cancer Research* 56:1098–1103 (1996).

Beaucage, S. and Caruthers, M., "Deoxynucleoside Phosphoramidites–A New Class of Key Intermediates for Deoxypolynucleotide Synthesis," *Tetrahedron Letters* 22(20):1859–1862 (1981).

Beaudet, A. and Tsui, L., "A Suggested Nomenclature for Designating Mutations," *Human Mutation* 2:245–248 (1993).

Bertwistle, D. and Ashworth, A., "Functions of the BRCA1 and BRCA2 genes,", *Curr. Opin. Genet. Dev.* 8(1):14–20 (1998).

Connor et al., "Detection of sickle cell $\beta^s$–globin allele by hydridization with synthetic oligonucleotides," *Proc. Natl. Acad. Sci. USA* 80:278–282 (1983).

Crooke, S., "Therapeutic Applictions of Oligonucleotides," *Annu. Rev. Pharmacol. Toxicol.* 32:329–376 (1992).

Easton et al., "Genetic Linkage Analysis in Familial Breast and Ovarian Cancer: Results from 214 Families," *American Journal of Human Genetics* 52:678–701 (1993).

Friend et al., "Breast cancer information on the web," *Nature Genetics* 11:238–239 (1995).

Holt et al., "Growth retardation and tumor inhibition by BRCA1," *Nature Genetics* 12:298–302 (1996).

Holt, M.D., J. and Arteaga, M.D., C., "BRCA1 Retroviral Gene Therapy for Ovarian Cancer," a Human Gene Transfer Protocol: NIH ORDA Registration#: 9603–149, pp. 1003–1030.

Husain et al., "BRCA1 Up–Regulation Is Associated with Repair–mediated Resistance to cis–Diamminedichloroplatinum(II)," *Cancer Res.* 58:1120–1123 (1998).

Jensen et al., "Characterization of Baculovirus–Expressed Human α and β Platelet–Derived Growth Factor Receptors," *Biochemistry* 31:10887–10892 (1992).

Jensen et al., "BRCA1 is secreted and exhibits properties of a granin," *Nat. Genetics* 12:303–308 (1996).

Landgren et al., "A Ligase–Mediated Gene Detection Technique," *Science* 241:1077–1080 (1988).

Landgren et al., "DNA Diagnostics—Molecular Techniques and Automation," *Science* 242:229–237 (1988).

Maniatis et al., "Molecular Cloning: A Laboratory Manual," Cold Spring Harbor Laboratory, NY, pp. 280–281 (1982).

Miki et al., "A Strong Candidate for the Breast and Ovarian Cancer Susceptibility Gene BRCA1," *Science* 266:66–71 (1994).

"PCR. A Practical Approach," ILR Press, Eds. M.J. McPherson, P. Quirke, and G.R. Taylor, Oxford University Press (1992).

Robinson–Benion, C. and Holt, J., "[23] Antisense Techniques," *Methods Enzymol.* 254:363–375 (1995).

Rowell et al., "Invited Editorial: Inherited Predisposition to Breast and Ovarian Cancer," *American Journal of Human Genetics* 55:861–865 (1994).

Ruffner et al., "BRCA1 is a cell cycle–regulated nuclear phosphoprotein," *Pro. Natl. Acad. Sci. USA* 94:7138–7143 (1997).

Saiki et al., "A Novel Method for the Detection of Polymorphic Restriction Sites by Cleavage of Oligonucleotide Probes: Application to Sickle–Cell Anemia," *Bio/Technology* 3:1008–1012 (1985).

Sambrook et al., "Molecular Cloning: A Laboratory Manual, Second Edition," Cold Spring Harbor Laboratory Press, Cold Spring Harbor, NY (1989).

Shattuck–Eidens et al., "BRCA1 Sequence Analysis in Women at High Risk for Susceptibility Mutations," *J. Am. Med. Assn.* 278(15):1242–1250 (1997).

Shuldiner et al., "Handbook of Endocrine Research Techniques," pp. 457–486, DePablo, F., Scanes, C., Weintraub, B., eds., Academic Press, Inc. (1993).

Thompson et al., "Decreased expression of BRCA1 accelerates growth and is often present during sporadic breast cancer progression," *Nature Genetics* 9:444–450 (1995).

Zhang et al., "BRCA1, BRCA2, and DNA Damage Response: Collision or Collusion?" *Cell* 92:433–436 (1998).

Grantham et al. (1981) Codon catalog usage is a genome strategy modulated for gene expressivity, Nucleic Acids Res. 9:r43–r74.

Rosenberg et al. (2000) Gene therapist, Heal thyself, Science 287:17–18.

* cited by examiner

SEQUENCE LISTING (1) GENERAL INFORMATION:

(iii) NUMBER OF SEQUENCES: 67

(2) INFORMATION FOR SEQ ID NO: 1:

(i) SEQUENCE CHARACTERISTICS:
       (A) LENGTH: 5711 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (vi) ORIGINAL SOURCE:
       (A) ORGANISM: HOMO SAPIENS
       (B) STRAIN: BRCA1
       (E) HAPLOTYPE: OMI4

(viii) POSITION IN GENOME:
       (A) CHROMOSOME/SEGMENT: 17
       (B) MAP POSITION: 17q21

(xi) SEQUENCE DESCRIPTION: SEQ ID NO: 1:

```
AGCTCGCTGA GACTTCCTGG ACCCCGCACC AGGCTGTGGG GTTTCTCAGA TAACTGGGCC      60
CCTGCGCTCA GGAGGCCTTC ACCCTCTGCT CTGGGTAAAG TTCATTGGAA CAGAAAGAAA     120
TGGATTTATC TGCTCTTCGC GTTGAAGAAG TACAAAATGT CATTAATGCT ATGCAGAAAA     180
TCTTAGAGTG TCCCATCTGT CTGGAGTTGA TCAAGGAACC TGTCTCCACA AAGTGTGACC     240
ACATATTTTG CAAATTTTGC ATGCTGAAAC TTCTCAACCA GAAGAAAGGG CCTTCACAGT     300
GTCCTTTATG TAAGAATGAT ATAACCAAAA GGAGCCTACA AGAAAGTACG AGATTTAGTC     360
AACTTGTTGA AGAGCTATTG AAAATCATTT GTGCTTTTCA GCTTGACACA GGTTTGGAGT     420
ATGCAAACAG CTATAATTTT GCAAAAAAGG AAAATAACTC TCCTGAACAT CTAAAAGATG     480
AAGTTTCTAT CATCCAAAGT ATGGGCTACA GAAACCGTGC CAAAAGACTT CTACAGAGTG     540
AACCCGAAAA TCCTTCCTTG CAGGAAACCA GTCTCAGTGT CCAACTCTCT AACCTTGGAA     600
CTGTGAGAAC TCTGAGGACA AAGCAGCGGA TACAACCTCA AAAGACGTCT GTCTACATTG     660
AATTGGGATC TGATTCTTCT GAAGATACCG TTAATAAGGC AACTTATTGC AGTGTGGGAG     720
ATCAAGAATT GTTACAAATC ACCCCTCAAG GAACCAGGGA TGAAATCAGT TTGGATTCTG     780
CAAAAAAGGC TGCTTGTGAA TTTTCTGAGA CGGATGTAAC AAATACTGAA CATCATCAAC     840
CCAGTAATAA TGATTTGAAC ACCACTGAGA AGCGTGCAGC TGAGAGGCAT CCAGAAAAGT     900
ATCAGGGTAG TTCTGTTTCA AACTTGCATG TGGAGCCATG TGGCACAAAT ACTCATGCCA     960
GCTCATTACA GCATGAGAAC AGCAGTTTAT TACTCACTAA AGACAGAATG AATGTAGAAA    1020
AGGCTGAATT CTGTAATAAA AGCAAACAGC CTGGCTTAGC AAGGAGCCAA CATAACAGAT    1080
GGGCTGGAAG TAAGGAAACA TGTAATGATA GGCGGACTCC CAGCACAGAA AAAAAGGTAG    1140
ATCTGAATGC TGATCCCCTG TGTGAGAGAA AGAATGGAA TAAGCAGAAA CTGCCATGCT    1200
CAGAGAATCC TAGAGATACT GAAGATGTTC CTTGGATAAC ACTAAATAGC AGCATTCAGA    1260
AAGTTAATGA GTGGTTTTCC AGAAGTGATG AACTGTTAGG TTCTGATGAC TCACATGATG    1320
```

```
GGGAGTCTGA ATCAAATGCC AAAGTAGCTG ATGTATTGGA CGTTCTAAAT GAGGTAGATG    1380

AATATTCTGG TTCTTCAGAG AAAATAGACT TACTGGCCAG TGATCCTCAT GAGGCTTTAA    1440

TATGTAAAAG TGAAAGAGTT CACTCCAAAT CAGTAGAGAG TAATATTGAA GACAAAATAT    1500

TTGGGAAAAC CTATCGGAAG AAGGCAAGCC TCCCCAACTT AAGCCATGTA ACTGAAAATC    1560

TAATTATAGG AGCATTTGTT ACTGAGCCAC AGATAATACA AGAGCGTCCC CTCACAAATA    1620

AATTAAAGCG TAAAAGGAGA CCTACATCAG GCCTTCATCC TGAGGATTTT ATCAAGAAAG    1680

CAGATTTGGC AGTTCAAAAG ACTCCTGAAA TGATAAATCA GGGAACTAAC CAAACGGAGC    1740

AGAATGGTCA AGTGATGAAT ATTACTAATA GTGGTCATGA GAATAAAACA AAAGGTGATT    1800

CTATTCAGAA TGAGAAAAAT CCTAACCCAA TAGAATCACT CGAAAAAGAA TCTGCTTTCA    1860

AAACGAAAGC TGAACCTATA AGCAGCAGTA TAAGCAATAT GGAACTCGAA TTAAATATCC    1920

ACAATTCAAA AGCACCTAAA AAGAATAGGC TGAGGAGGAA GTCTTCTACC AGGCATATTC    1980

ATGCGCTTGA ACTAGTAGTC AGTAGAAATC TAAGCCCACC TAATTGTACT GAATTGCAAA    2040

TTGATAGTTG TTCTAGCAGT GAAGAGATAA AGAAAAAAAA GTACAACCAA ATGCCAGTCA    2100

GGCACAGCAG AAACCTACAA CTCATGGAAG GTAAAGAACC TGCAACTGGA GCCAAGAAGA    2160

GTAACAAGCC AAATGAACAG ACAAGTAAAA GACATGACAG TGATACTTTC CCAGAGCTGA    2220

AGTTAACAAA TGCACCTGGT TCTTTTACTA AGTGTTCAAA TACCAGTGAA CTTAAAGAAT    2280

TTGTCAATCC TAGCCTTCCA AGAGAAGAAA AAGAAGAGAA ACTAGAAACA GTTAAAGTGT    2340

CTAATAATGC TGAAGACCCC AAAGATCTCA TGTTAAGTGG AGAAAGGGTT TTGCAAACTG    2400

AAAGATCTGT AGAGAGTAGC AGTATTTCAC TGGTACCTGG TACTGATTAT GGCACTCAGG    2460

AAAGTATCTC GTTACTGGAA GTTAGCACTC TAGGGAAGGC AAAAACAGAA CCAAATAAAT    2520

GTGTGAGTCA GTGTGCAGCA TTTGAAAACC CCAAGGGACT AATTCATGGT TGTTCCAAAG    2580

ATAATAGAAA TGACACAGAA GGCTTTAAGT ATCCATTGGG ACATGAAGTT AACCACAGTC    2640

GGGAAACAAG CATAGAAATG GAAGAAAGTG AACTTGATGC TCAGTATTTG CAGAATACAT    2700

TCAAGGTTTC AAAGCGCCAG TCATTTGCTC TGTTTTCAAA TCCAGGAAAT GCAGAAGAGG    2760

AATGTGCAAC ATTCTCTGCC CACTCTGGGT CCTTAAAGAA ACAAAGTCCA AAAGTCACTT    2820

TTGAATGTGA ACAAAAGGAA GAAAATCAAG GAAAGAATGA GTCTAATATC AAGCCTGTAC    2880

AGACAGTTAA TATCACTGCA GGCTTTCCTG TGGTTGGTCA GAAAGATAAG CCAGTTGATA    2940

ATGCCAAATG TAGTATCAAA GGAGGCTCTA GGTTTTGTCT ATCATCTCAG TTCAGAGGCA    3000

ACGAAACTGG ACTCATTACT CCAAATAAAC ATGGACTTTT ACAAAACCCA TATCGTATAC    3060

CACCACTTTT TCCCATCAAG TCATTTGTTA AAACTAAATG TAAGAAAAAT CTGCTAGAGG    3120

AAAACTTTGA GGAACATTCA ATGTCACCTG AAAGAGAAAT GGGAAATGAG AACATTCCAA    3180

GTACAGTGAG CACAATTAGC CGTAATAACA TTAGAGAAAA TGTTTTTAAA GAAGCCAGCT    3240

CAAGCAATAT TAATGAAGTA GGTTCCAGTA CTAATGAAGT GGGCTCCAGT ATTAATGAAA    3300

TAGGTTCCAG TGATGAAAAC ATTCAAGCAG AACTAGGTAG AAACAGAGGG CCAAAATTGA    3360

ATGCTATGCT TAGATTAGGG GTTTTGCAAC CTGAGGTCTA TAAACAAAGT CTTCCTGGAA    3420

GTAATTGTAA GCATCCTGAA ATAAAAAAGC AAGAATATGA AGAAGTAGTT CAGACTGTTA    3480

ATACAGATTT CTCTCCATAT CTGATTTCAG ATAACTTAGA ACAGCCTATG GGAAGTAGTC    3540

ATGCATCTCA GGTTTGTTCT GAGACACCTG ATGACCTGTT AGATGATGGT GAAATAAAGG    3600

AAGATACTAG TTTTGCTGAA AATGACATTA AGGAAAGTTC TGCTGTTTTT AGCAAAAGCG    3660

TCCAGAGAGG AGAGCTTAGC AGGAGTCCTA GCCCTTTCAC CCATACACAT TTGGCTCAGG    3720
```

-continued

```
GTTACCGAAG AGGGGCCAAG AAATTAGAGT CCTCAGAAGA GAACTTATCT AGTGAGGATG    3780

AAGAGCTTCC CTGCTTCCAA CACTTGTTAT TTGGTAAAGT AAACAATATA CCTTCTCAGT    3840

CTACTAGGCA TAGCACCGTT GCTACCGAGT GTCTGTCTAA GAACACAGAG GAGAATTTAT    3900

TATCATTGAA GAATAGCTTA AATGACTGCA GTAACCAGGT AATATTGGCA AAGGCATCTC    3960

AGGAACATCA CCTTAGTGAG GAAACAAAAT GTTCTGCTAG CTTGTTTTCT TCACAGTGCA    4020

GTGAATTGGA AGACTTGACT GCAAATACAA ACACCCAGGA TCCTTTCTTG ATTGGTTCTT    4080

CCAAACAAAT GAGGCATCAG TCTGAAAGCC AGGGAGTTGG TCTGAGTGAC AAGGAATTGG    4140

TTTCAGATGA TGAAGAAAGA GGAACGGGCT TGGAAGAAAA TAATCAAGAA GAGCAAAGCA    4200

TGGATTCAAA CTTAGGTGAA GCAGCATCTG GGTGTGAGAG TGAAACAAGC GTCTCTGAAG    4260

ACTGCTCAGG GCTATCCTCT CAGAGTGACA TTTTAACCAC TCAGCAGAGG GATACCATGC    4320

AACATAACCT GATAAAGCTC CAGCAGGAAA TGGCTGAACT AGAAGCTGTG TTAGAACAGC    4380

ATGGGAGCCA GCCTTCTAAC AGCTACCCTT CCATCATAAG TGACTCCTCT GCCCTTGAGG    4440

ACCTGCGAAA TCCAGAACAA AGCACATCAG AAAAAGCAGT ATTAACTTCA CAGAAAAGTA    4500

GTGAATACCC TATAAGCCAG AATCCAGAAG GCCTTTCTGC TGACAAGTTT GAGGTGTCTG    4560

CAGATAGTTC TACCAGTAAA AATAAAGAAC CAGGAGTGGA AAGGTCATCC CCTTCTAAAT    4620

GCCCATCATT AGATGATAGG TGGTACATGC ACAGTTGCTC TGGGAGTCTT CAGAATAGAA    4680

ACTACCCATC TCAAGAGGAG CTCATTAAGG TTGTTGATGT GGAGGAGCAA CAGCTGGAAG    4740

AGTCTGGGCC ACACGATTTG ACGGAAACAT CTTACTTGCC AAGGCAAGAT CTAGAGGGAA    4800

CCCCTTACCT GGAATCTGGA ATCAGCCTCT TCTCTGATGA CCCTGAATCT GATCCTTCTG    4860

AAGACAGAGC CCCAGAGTCA GCTCGTGTTG GCAACATACC ATCTTCAACC TCTGCATTGA    4920

AAGTTCCCCA ATTGAAAGTT GCAGAATCTG CCCAGGGTCC AGCTGCTGCT CATACTACTG    4980

ATACTGCTGG GTATAATGCA ATGGAAGAAA GTGTGAGCAG GGAGAAGCCA GAATTGACAG    5040

CTTCAACAGA AAGGGTCAAC AAAAGAATGT CCATGGTGGT GTCTGGCCTG ACCCCAGAAG    5100

AATTTATGCT CGTGTACAAG TTTGCCAGAA ACACCACAT CACTTTAACT AATCTAATTA    5160

CTGAAGAGAC TACTCATGTT GTTATGAAAA CAGATGCTGA GTTTGTGTGT AACGGACAC    5220

TGAAATATTT TCTAGGAATT GCGGGAGGAA AATGGGTAGT TAGCTATTTC TGGGTGACCC    5280

AGTCTATTAA AGAAAGAAAA ATGCTGAATG AGCATGATTT TGAAGTCAGA GGAGATGTGG    5340

TCAATGGAAG AAACCACCAA GGTCCAAAGC GAGCAAGAGA ATCCCAGGAC AGAAAGATCT    5400

TCAGGGGGCT AGAAATCTGT TGCTATGGGC CCTTCACCAA CATGCCCACA GATCAACTGG    5460

AATGGATGGT ACAGCTGTGT GGTGCTTCTG TGGTGAAGGA GCTTTCATCA TTCACCCTTG    5520

GCACAGGTGT CCACCCAATT GTGGTTGTGC AGCCAGATGC CTGGACAGAG GACAATGGCT    5580

TCCATGCAAT TGGGCAGATG TGTGAGGCAC CTGTGGTGAC CCGAGAGTGG GTGTTGGACA    5640

GTGTAGCACT CTACCAGTGC CAGGAGCTGG ACACCTACCT GATACCCCAG ATCCCCCACA    5700

GCCACTACTG A                                                         5711
```

(2) INFORMATION FOR SEQ ID NO: 2:

(i) SEQUENCE CHARACTERISTICS:
        (A) LENGTH: 1863 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
             (A) ORGANISM: HOMO SAPIENS
             (B) STRAIN: BRCA1
             (E) HAPLOTYPE: OMI4

(viii) POSITION IN GENOME:
             (A) CHROMOSOME/SEGMENT: 17
             (B) MAP POSITION: 17q21

(xi) SEQUENCE DESCRIPTION: SEQ ID NO: 2:

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
                35                  40                  45

Leu Lys Leu Leu Asn Gln Lys Lys Gly Pro Ser Gln Cys Pro Leu Cys
50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
                100                 105                 110

Asn Ser Pro Glu His Leu Lys Asp Glu Val Ser Ile Ile Gln Ser Met
            115                 120                 125

Gly Tyr Arg Asn Arg Ala Lys Arg Leu Leu Gln Ser Glu Pro Glu Asn
            130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
                180                 185                 190

Lys Ala Thr Tyr Cys Ser Val Gly Asp Gln Glu Leu Leu Gln Ile Thr
            195                 200                 205

Pro Gln Gly Thr Arg Asp Glu Ile Ser Leu Asp Ser Ala Lys Lys Ala
210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
            245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
            275                 280                 285

Ser Leu Leu Leu Thr Lys Asp Arg Met Asn Val Glu Lys Ala Glu Phe
            290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr

```
                    325                 330                 335
Glu Lys Lys Val Asp Leu Asn Ala Asp Pro Leu Cys Glu Arg Lys Glu
            340                 345                 350
Trp Asn Lys Gln Lys Leu Pro Cys Ser Glu Asn Pro Arg Asp Thr Glu
            355                 360                 365
Asp Val Pro Trp Ile Thr Leu Asn Ser Ser Ile Gln Lys Val Asn Glu
    370                 375                 380
Trp Phe Ser Arg Ser Asp Glu Leu Leu Gly Ser Asp Asp Ser His Asp
385                 390                 395                 400
Gly Glu Ser Glu Ser Asn Ala Lys Val Ala Asp Val Leu Asp Val Leu
                405                 410                 415
Asn Glu Val Asp Glu Tyr Ser Gly Ser Ser Glu Lys Ile Asp Leu Leu
            420                 425                 430
Ala Ser Asp Pro His Glu Ala Leu Ile Cys Lys Ser Glu Arg Val His
            435                 440                 445
Ser Lys Ser Val Glu Ser Asn Ile Glu Asp Lys Ile Phe Gly Lys Thr
    450                 455                 460
Tyr Arg Lys Lys Ala Ser Leu Pro Asn Leu Ser His Val Thr Glu Asn
465                 470                 475                 480
Leu Ile Ile Gly Ala Phe Val Thr Glu Pro Gln Ile Ile Gln Glu Arg
                485                 490                 495
Pro Leu Thr Asn Lys Leu Lys Arg Lys Arg Arg Pro Thr Ser Gly Leu
            500                 505                 510
His Pro Glu Asp Phe Ile Lys Lys Ala Asp Leu Ala Val Gln Lys Thr
            515                 520                 525
Pro Glu Met Ile Asn Gln Gly Thr Asn Gln Thr Glu Gln Asn Gly Gln
    530                 535                 540
Val Met Asn Ile Thr Asn Ser Gly His Glu Asn Lys Thr Lys Gly Asp
545                 550                 555                 560
Ser Ile Gln Asn Glu Lys Asn Pro Asn Pro Ile Glu Ser Leu Glu Lys
                565                 570                 575
Glu Ser Ala Phe Lys Thr Lys Ala Glu Pro Ile Ser Ser Ser Ile Ser
            580                 585                 590
Asn Met Glu Leu Glu Leu Asn Ile His Asn Ser Lys Ala Pro Lys Lys
            595                 600                 605
Asn Arg Leu Arg Arg Lys Ser Ser Thr Arg His Ile His Ala Leu Glu
    610                 615                 620
Leu Val Val Ser Arg Asn Leu Ser Pro Pro Asn Cys Thr Glu Leu Gln
625                 630                 635                 640
Ile Asp Ser Cys Ser Ser Ser Glu Glu Ile Lys Lys Lys Lys Tyr Asn
                645                 650                 655
Gln Met Pro Val Arg His Ser Arg Asn Leu Gln Leu Met Glu Gly Lys
            660                 665                 670
Glu Pro Ala Thr Gly Ala Lys Lys Ser Asn Lys Pro Asn Glu Gln Thr
    675                 680                 685
Ser Lys Arg His Asp Ser Asp Thr Phe Pro Glu Leu Lys Leu Thr Asn
    690                 695                 700
Ala Pro Gly Ser Phe Thr Lys Cys Ser Asn Thr Ser Glu Leu Lys Glu
705                 710                 715                 720
Phe Val Asn Pro Ser Leu Pro Arg Glu Glu Lys Glu Glu Lys Leu Glu
                725                 730                 735
Thr Val Lys Val Ser Asn Asn Ala Glu Asp Pro Lys Asp Leu Met Leu
            740                 745                 750
```

-continued

```
Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
        770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
                820                 825                 830

Leu Gly His Glu Val Asn His Ser Arg Glu Thr Ser Ile Glu Met Glu
                835                 840                 845

Glu Ser Glu Leu Asp Ala Gln Tyr Leu Gln Asn Thr Phe Lys Val Ser
        850                 855                 860

Lys Arg Gln Ser Phe Ala Leu Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
                900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
        930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
                980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val Ser
        1010                1015                1020

Thr Ile Ser Arg Asn Asn Ile Arg Glu Asn Val Phe Lys Gly Ala Ser
1025                1030                1035                1040

Ser Ser Asn Ile Asn Glu Val Gly Ser Ser Thr Asn Glu Val Gly Ser
                1045                1050                1055

Ser Ile Asn Glu Ile Gly Ser Ser Asp Glu Asn Ile Gln Ala Glu Leu
                1060                1065                1070

Gly Arg Asn Arg Glu Pro Lys Leu Asn Ala Met Leu Arg Leu Gly Val
                1075                1080                1085

Leu Gln Pro Glu Val Tyr Lys Gln Ser Leu Pro Gly Ser Asn Cys Lys
        1090                1095                1100

His Pro Glu Ile Lys Lys Gln Glu Tyr Glu Glu Val Val Gln Thr Val
1105                1110                1115                1120

Asn Thr Asp Phe Ser Pro Tyr Leu Ile Ser Asp Asn Leu Glu Gln Pro
                1125                1130                1135

Met Gly Ser Ser His Ala Ser Gln Val Cys Ser Glu Thr Pro Asp Asp
                1140                1145                1150

Leu Leu Asp Asp Gly Glu Ile Lys Glu Asp Thr Ser Phe Ala Glu Asn
                1155                1160                1165
```

```
-continued

Asp Ile Lys Glu Ser Ser Ala Val Phe Ser Lys Ser Val Gln Arg Gly
    1170                1175                1180

Glu Leu Ser Arg Ser Pro Ser Pro Phe Thr His Thr His Leu Ala Gln
1185                1190                1195                1200

Gly Tyr Arg Arg Gly Ala Lys Lys Leu Glu Ser Ser Glu Glu Asn Leu
        1205                1210                1215

Ser Ser Glu Asp Glu Glu Leu Pro Cys Phe Gln His Leu Leu Phe Gly
        1220                1225                1230

Lys Val Asn Asn Ile Pro Ser Gln Ser Thr Arg His Ser Thr Val Ala
            1235                1240                1245

Thr Glu Cys Leu Ser Lys Asn Thr Glu Glu Asn Leu Leu Ser Leu Lys
    1250                1255                1260

Asn Ser Leu Asn Asp Cys Ser Asn Gln Val Ile Leu Ala Lys Ala Ser
1265                1270                1275                1280

Gln Glu His His Leu Ser Glu Glu Thr Lys Cys Ser Ala Ser Leu Phe
        1285                1290                1295

Ser Ser Gln Cys Ser Glu Leu Glu Asp Leu Thr Ala Asn Thr Asn Thr
        1300                1305                1310

Gln Asp Pro Phe Leu Ile Gly Ser Ser Lys Gln Met Arg His Gln Ser
    1315                1320                1325

Glu Ser Gln Gly Val Gly Leu Ser Asp Lys Glu Leu Val Ser Asp Asp
    1330                1335                1340

Glu Glu Arg Gly Thr Gly Leu Glu Glu Asn Asn Gln Glu Glu Gln Ser
1345                1350                1355                1360

Met Asp Ser Asn Leu Gly Glu Ala Ala Ser Gly Cys Glu Ser Glu Thr
        1365                1370                1375

Ser Val Ser Glu Asp Cys Ser Gly Leu Ser Ser Gln Ser Asp Ile Leu
        1380                1385                1390

Thr Thr Gln Gln Arg Asp Thr Met Gln His Asn Leu Ile Lys Leu Gln
    1395                1400                1405

Gln Glu Met Ala Glu Leu Glu Ala Val Leu Glu Gln His Gly Ser Gln
    1410                1415                1420

Pro Ser Asn Ser Tyr Pro Ser Ile Ile Ser Asp Ser Ser Ala Leu Glu
1425                1430                1435                1440

Asp Leu Arg Asn Pro Glu Gln Ser Thr Ser Glu Lys Ala Val Leu Thr
        1445                1450                1455

Ser Gln Lys Ser Ser Glu Tyr Pro Ile Ser Gln Asn Pro Glu Gly Leu
        1460                1465                1470

Ser Ala Asp Lys Phe Glu Val Ser Ala Asp Ser Ser Thr Ser Lys Asn
    1475                1480                1485

Lys Glu Pro Gly Val Glu Arg Ser Ser Pro Ser Lys Cys Pro Ser Leu
    1490                1495                1500

Asp Asp Arg Trp Tyr Met His Ser Cys Ser Gly Ser Leu Gln Asn Arg
1505                1510                1515                1520

Asn Tyr Pro Ser Gln Glu Glu Leu Ile Lys Val Val Asp Val Glu Glu
        1525                1530                1535

Gln Gln Leu Glu Glu Ser Gly Pro His Asp Leu Thr Glu Thr Ser Tyr
        1540                1545                1550

Leu Pro Arg Gln Asp Leu Glu Gly Thr Pro Tyr Leu Glu Ser Gly Ile
    1555                1560                1565

Ser Leu Phe Ser Asp Asp Pro Glu Ser Asp Pro Ser Glu Asp Arg Ala
    1570                1575                1580

Pro Glu Ser Ala Arg Val Gly Asn Ile Pro Ser Ser Thr Ser Ala Leu
```

1585               1590               1595               1600

Lys Val Pro Gln Leu Lys Val Ala Glu Ser Ala Gln Gly Pro Ala Ala
                 1605                1610                1615

Ala His Thr Thr Asp Thr Ala Gly Tyr Asn Ala Met Glu Glu Ser Val
            1620                1625                1630

Ser Arg Glu Lys Pro Glu Leu Thr Ala Ser Thr Glu Arg Val Asn Lys
       1635                1640                1645

Arg Met Ser Met Val Val Ser Gly Leu Thr Pro Glu Glu Phe Met Leu
  1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
                 1685                1690                1695

Cys Glu Arg Thr Leu Lys Tyr Phe Leu Gly Ile Ala Gly Gly Lys Trp
            1700                1705                1710

Val Val Ser Tyr Phe Trp Val Thr Gln Ser Ile Lys Glu Arg Lys Met
       1715                1720                1725

Leu Asn Glu His Asp Phe Glu Val Arg Gly Asp Val Val Asn Gly Arg
  1730                1735                1740

Asn His Gln Gly Pro Lys Arg Ala Arg Glu Ser Gln Asp Arg Lys Ile
1745                1750                1755                1760

Phe Arg Gly Leu Glu Ile Cys Cys Tyr Gly Pro Phe Thr Asn Met Pro
                 1765                1770                1775

Thr Asp Gln Leu Glu Trp Met Val Gln Leu Cys Gly Ala Ser Val Val
            1780                1785                1790

Lys Glu Leu Ser Ser Phe Thr Leu Gly Thr Gly Val His Pro Ile Val
       1795                1800                1805

Val Val Gln Pro Asp Ala Trp Thr Glu Asp Asn Gly Phe His Ala Ile
  1810                1815                1820

Gly Gln Met Cys Glu Ala Pro Val Val Thr Arg Glu Trp Val Leu Asp
1825                1830                1835                1840

Ser Val Ala Leu Tyr Gln Cys Gln Glu Leu Asp Thr Tyr Leu Ile Pro
                 1845                1850                1855

Gln Ile Pro His Ser His Tyr
            1860

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 3:

GAAGTTGTCA TTTTATAAAC CTTT                                                    24

(2) INFORMATION FOR SEQ ID NO: 4:

(i) SEQUENCE CHARACTERISTICS:

(A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 4:

TGTCTTTTCT TCCCTAGTAT G                                              21

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 5:

TCCTGACACA GCAGACATTT A                                              21

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 6:

TTGGATTTTC GTTCTCACTT A                                              21

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 7:

CTCTTAAGGG CAGTTGTGAG                                                         20

(2) INFORMATION FOR SEQ ID NO: 8:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 8:

TTCCTACTGT GGTTGCTTCC                                                         20

(2) INFORMATION FOR SEQ ID NO: 9:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 9:

CTTATTTTAG TGTCCTTAAA AGG                                                     23

(2) INFORMATION FOR SEQ ID NO: 10:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(iii) HYPOTHETICAL: NO (iv) ANTI-SENSE: NO (v) FRAGMENT TYPE: internal (xi) SEQUENCE DESCRIPTION: SEQ ID NO: 10:

TTTCATGGAC AGCACTTGAG TG                                                      22

(2) INFORMATION FOR SEQ ID NO: 11:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
             (A) DESCRIPTION: /desc = "primer"

(iii) HYPOTHETICAL: NO (iv) ANTI-SENSE: NO (v) FRAGMENT TYPE: internal (xi) SEQUENCE DESCRIPTION: SEQ ID NO: 11:

CACAACAAAG AGCATACATA GGG                                               23

(2) INFORMATION FOR SEQ ID NO: 12:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(iii) HYPOTHETICAL: NO (iv) ANTI-SENSE: NO (v) FRAGMENT TYPE: internal (xi) SEQUENCE DESCRIPTION: SEQ ID NO: 12:

TCGGGTTCAC TCTGTAGAAG                                                   20

(2) INFORMATION FOR SEQ ID NO: 13:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(iii) HYPOTHETICAL: NO (iv) ANTI-SENSE: NO (v) FRAGMENT TYPE: internal (xi) SEQUENCE DESCRIPTION: SEQ ID NO: 13:

TTCTCTTCAG GAGGAAAAGC A                                                 21

(2) INFORMATION FOR SEQ ID NO: 14:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "primer"

(iii) HYPOTHETICAL: NO (iv) ANTI-SENSE: NO (v) FRAGMENT TYPE: internal (xi) SEQUENCE DESCRIPTION: SEQ ID NO: 14:

GCTGCCTACC ACAAATACAA A                                                 21

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iii) HYPOTHETICAL: NO (iv) ANTI-SENSE: NO (v) FRAGMENT TYPE: internal (xi) SEQUENCE DESCRIPTION: SEQ ID NO: 15:

CCACAGTAGA TGCTCAGTAA ATA                         23

(2) INFORMATION FOR SEQ ID NO: 16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iii) HYPOTHETICAL: NO (iv) ANTI-SENSE: NO (v) FRAGMENT TYPE: internal (xi) SEQUENCE DESCRIPTION: SEQ ID NO: 16:

TAGGAAAATA CCAGCTTCAT AGA                         23

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iii) HYPOTHETICAL: NO (iv) ANTI-SENSE: NO (v) FRAGMENT TYPE: internal (xi) SEQUENCE DESCRIPTION: SEQ ID NO: 17:

TGGTCAGCTT TCTGTAATCG                            20

(2) INFORMATION FOR SEQ ID NO: 18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 18:

GTATCTACCC ACTCTCTTCA G                                              21

(2) INFORMATION FOR SEQ ID NO: 19:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 19:

CCACCTCCAA GGTGTATCA                                                 19

(2) INFORMATION FOR SEQ ID NO: 20:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 20:

TGTTATGTTG GCTCCTTGCT                                                20

(2) INFORMATION FOR SEQ ID NO: 21:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 21:

CACTAAAGAC AGAATGAATC TA                                             22

(2) INFORMATION FOR SEQ ID NO: 22:

```
    (i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 22:

GAAGAACCAG AATATTCATC TA                                               22

(2) INFORMATION FOR SEQ ID NO: 23:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 23:

TGATGGGGAG TCTGAATCAA                                                  20

(2) INFORMATION FOR SEQ ID NO: 24:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 24:

TCTGCTTTCT TGATAAAATC CT                                               22

(2) INFORMATION FOR SEQ ID NO: 25:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PRIMER"

(iii) HYPOTHETICAL: NO (iv) ANTI-SENSE: NO
```

(v) FRAGMENT TYPE: internal (xi) SEQUENCE DESCRIPTION: SEQ ID NO: 25:

AGCGTCCCCT CACAAATAAA                                                    20

(2) INFORMATION FOR SEQ ID NO: 26:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 26:

TCAAGCGCAT GAATATGCCT                                                    20

(2) INFORMATION FOR SEQ ID NO: 27:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 27:

GTATAAGCAA TATGGAACTC GA                                                 22

(2) INFORMATION FOR SEQ ID NO: 28:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 28:

TTAAGTTCAC TGGTATTTGA ACA                                                23

(2) INFORMATION FOR SEQ ID NO: 29:

(i) SEQUENCE CHARACTERISTICS:
            (A) LENGTH: 20 base pairs
            (B) TYPE: nucleic acid
            (C) STRANDEDNESS: single (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 29:

GACAGCGATA CTTTCCCAGA                                                   20

(2) INFORMATION FOR SEQ ID NO: 30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 30:

TGGAACAACC ATGAATTAGT C                                                 21

(2) INFORMATION FOR SEQ ID NO: 31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 31:

GGAAGTTAGC ACTCTAGGGA                                                   20

(2) INFORMATION FOR SEQ ID NO: 32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 32:

TGGGTCCTTA AAGAAACAAA GT                                                    22

(2) INFORMATION FOR SEQ ID NO: 33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 33:

TCAGGTGACA TTGAATCTTC C                                                     21

(2) INFORMATION FOR SEQ ID NO: 34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 34:

CCACTTTTTC CCATCAAGTC A                                                     21

(2) INFORMATION FOR SEQ ID NO: 35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 35:

TCAGGATGCT TACAATTACT TC                                                    22

(2) INFORMATION FOR SEQ ID NO: 36:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 36:

CAAAATTGAA TGCTATGCTT AGA                                                   23

(2) INFORMATION FOR SEQ ID NO: 37:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 37:

TCGGTAACCC TGAGCCAAAT                                                       20

(2) INFORMATION FOR SEQ ID NO: 38:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 38:

GCAAAAGCGT CCAGAAAGGA                                                       20

(2) INFORMATION FOR SEQ ID NO: 39:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 39:

TATTTGCAGT CAAGTCTTCC AA                                                    22

(2) INFORMATION FOR SEQ ID NO: 40:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 40:

GTAATATTGG CAAAGGCATC T                                            21

(2) INFORMATION FOR SEQ ID NO: 41:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 41:

TAAAATGTGC TCCCCAAAAG CA                                           22

(2) INFORMATION FOR SEQ ID NO: 42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 42:

GTCCTGCCAA TGAGAAGAAA                                              20

(2) INFORMATION FOR SEQ ID NO: 43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 43:

TGTCAGCAAA CCTAAGAATG T                                                             21

(2) INFORMATION FOR SEQ ID NO: 44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 44:

AATGGAAAGC TTCTCAAAGT A                                                             21

(2) INFORMATION FOR SEQ ID NO: 45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 45:

ATGTTGGAGC TAGGTCCTTA C                                                             21

(2) INFORMATION FOR SEQ ID NO: 46:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 46:

CTAACCTGAA TTATCACTAT CA                                                            22

(2) INFORMATION FOR SEQ ID NO: 47:

(i) SEQUENCE CHARACTERISTICS:
        (A) LENGTH: 21 base pairs
        (B) TYPE: nucleic acid (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 47:

GTGTATAAAT GCCTGTATGC A                                                  21

(2) INFORMATION FOR SEQ ID NO: 48:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 48:

TGGCTGCCCA GGAAGTATG                                                     19

(2) INFORMATION FOR SEQ ID NO: 49:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 49:

AACCAGAATA TCTTTATGTA GGA                                                23

(2) INFORMATION FOR SEQ ID NO: 50:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 50:

AATTCTTAAC AGAGACCAGA AC                                              22

(2) INFORMATION FOR SEQ ID NO: 51:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 51:

AAAACTCTTT CCAGAATGTT GT                                              22

(2) INFORMATION FOR SEQ ID NO: 52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 52:

GTGTAGAACG TGCAGGATTG                                                 20

(2) INFORMATION FOR SEQ ID NO: 53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 53:

TCGCCTCATG TGGTTTTA                                                   18

(2) INFORMATION FOR SEQ ID NO: 54:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid -continued (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 54:

GGCTCTTTAG CTTCTTAGGA C                                    21

(2) INFORMATION FOR SEQ ID NO: 55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 55:

GAGACCATTT TCCCAGCATC                                      20

(2) INFORMATION FOR SEQ ID NO: 56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 56:

CTGTCATTCT TCCTGTGCTC                                      20

(2) INFORMATION FOR SEQ ID NO: 57:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 57:

CATTGTTAAG GAAAGTGGTG C                                    21

(2) INFORMATION FOR SEQ ID NO: 58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 58:

ATATGACGTG TCTGCTCCAC                                                        20

(2) INFORMATION FOR SEQ ID NO: 59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 59:

GGGAATCCAA ATTACACAGC                                                        20

(2) INFORMATION FOR SEQ ID NO: 60:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 60:

AAGCTCTTCT TTGAAAGTC                                                         19

(2) INFORMATION FOR SEQ ID NO: 61:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 61:

GTAGAGAAAT AGAATAGCCT CT                                                    22

(2) INFORMATION FOR SEQ ID NO: 62:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 62:

TCCCATTGAG AGGTCTTGCT                                                       20

(2) INFORMATION FOR SEQ ID NO: 63:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 63:

GAGAAGACTT CTGAGGCTAC                                                       20

(2) INFORMATION FOR SEQ ID NO: 64:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 64:

TGAAGTGACA GTTCCAGTAG T                                                     21

(2) INFORMATION FOR SEQ ID NO: 65:

(i) SEQUENCE CHARACTERISTICS:
            (A) LENGTH: 23 base pairs

-continued

```
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 65:

CATTTTAGCC ATTCATTCAA CAA                                              23

(2) INFORMATION FOR SEQ ID NO: 66:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 66:

ATGAATTGAC ACTAATCTCT GC                                               22

(2) INFORMATION FOR SEQ ID NO: 67:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (xi) SEQUENCE DESCRIPTION: SEQ ID NO: 67:

GTAGCCAGGA CAGTAGAAGG A                                                21
```

CODING SEQUENCE HAPLOTYPE OF THE HUMAN BRCA1 GENE

This is a divisional application of co-pending application Ser. No. 09/074,452 (filed on May 6, 1998) now abandoned, all of which is incorporated herein by reference in its entirety.

FIELD OF THE INVENTION

This invention relates to a gene which has been associated with breast and ovarian cancer where the gene is found to be mutated. More specifically, this invention relates to a coding sequence of the BRCA1 gene, BRCA1(omi4), isolated from human subjects which defines a new haplotype.

BACKGROUND OF THE INVENTION

It has been estimated that about 5–10% of breast cancer is inherited Rowell, et al., *American Journal of Human Genetics*, 55:861–865 (1994). Located on chromosome 17, BRCA1 is the first gene identified to be conferring increased risk for breast and ovarian cancer. Miki et al., *Science*, 266:66–71 (1994). Mutations in this "tumor suppressor" gene are thought to account for roughly 45% of inherited breast cancer and 80–90% of families with increased risk of early onset breast and ovarian cancer. Easton et al., *American Journal of Human Genetics*, 52:678–701 (1993).

Locating one or more mutations in the BRCA1 region of chromosome 17 provides a promising approach to reducing the high incidence and mortality associated with breast and ovarian cancer through the early detection of women at high risk. These women, once identified, can be targeted for more aggressive prevention programs. Screening is carried out by a variety of methods which include karyotyping, probe binding and DNA sequencing.

In DNA sequencing technology, genomic DNA is extracted from whole blood and the coding sequences of the BRCA1 gene are amplified. The coding sequences might be sequenced completely and the results are compared to the DNA sequence of the gene. Alternatively, the coding sequence of the sample gene may be compared to a panel of known mutations or other screening procedure before completely sequencing the gene and comparing it to a normal sequence of the gene.

If a mutation in the BRCA1 coding sequence is found, it may be possible to provide the individual with increased expression of the gene through gene transfer therapy. It has been demonstrated that the gene transfer of the BRCA1 coding sequence into cancer cells inhibits their growth and reduces tumorigenesis of human cancer cells in nude mice. Jeffrey Holt and his colleagues conclude that the product of BRCA1 expression is a secreted tumor growth inhibitor, making BRCA1 an ideal gene for gene therapy studies. Transduction of only a moderate percentage of tumor cells apparently produces enough growth inhibitor to inhibit all tumor cells. Arteaga and Holt, *Cancer Research*, 56: 1098–1103 (1996), Holt, et al., *Nature Genetics*, 12: 298–302 (1996). The observation of Holt et al, that the BRCA1 growth inhibitor is a secreted protein leads to the possible use of infection of the BRCA1 growth inhibitor into the area of the tumor for tumor suppression.

The BRCA1 gene is divided into 24 separate exons. Exons 1 and 4 are noncoding, in that they are not part of the final functional BRCA1 protein product. The BRCA1 coding sequence spans roughly 5600 base pairs (bp). Each exon consists of 200–400 bp, except for exon 11 which contains about 3600 bp. To sequence the coding sequence of the BRCA1 gene, each exon is amplified separately and the resulting PCR products are sequenced in the forward and reverse directions. Because exon 11 is so large, we have divided it into twelve overlapping PCR fragments of roughly 350 bp each (segments "A" through "L" of BRCA1 exon 11).

Many mutations and polymorphisms have already been reported in the BRCA1 gene. A world wide web site has been built to facilitate the detection and characterization of alterations in breast cancer susceptibility genes. Such mutations in BRCA1 can be accessed through the Breast Cancer Information Core (BIC) at: www.nchgr.nih.gov/dir/lab_transfer/bic. This data site became publicly available on Nov. 1, 1995. Friend, et al. *Nature Genetics*, 11:238, (1995).

The genetics of Breast/Ovarian Cancer Syndrome is autosomal dominant with reduced penetrance. In simple terms, this means that the syndrome runs through families: (1) both sexes can be carriers (mostly women get the disease but men can both pass it on and occasionally get breast cancer); (2) most generations will likely have breast cancer; (3) occasionally women carriers either die young before they have the time to manifest disease (and yet have offspring who get it) or they never develop breast or ovarian cancer and die of old age (the latter people are said to have "reduced penetrance" because they never develop cancer). Pedigree analysis and genetic counseling is absolutely essential to the proper workup of a family prior to any lab work.

Until recently, only a single coding sequence for the BRCA1 gene has been available for comparison to patient samples. That sequence is available as GENBANK Accession Number U14680. Recently another sequence has been made known in U.S. Pat. No. 5,654,155. There is a need in the art, to have available a coding sequence which is the BRCA1 coding sequence found in a portion of the normal population in order to determine whether or not a patient's BRCA1 gene sequence is mutant with increased susceptibility for cancer or a different normal sequence with no such succeptability. This will make it possible for true mutations to be easily identified or differentiated from naturally occurring sequence variations such as polymorphisms. Identification of mutations of the BRCA1 gene and protein allow more widespread diagnostic screening for hereditary breast and ovarian cancer than is currently possible and also have utility in gene therapy, protein replacement therapy and diagnosis.

Knowing the coding sequences which do not represent a higher susceptibility to an individual for cancer will reduce the likelihood of misinterpreting a "sequence variation" found in the population (i.e. polymorphism) with a pathologic "mutation" (i.e. causes disease in the individual or puts the individual at a high risk of developing the disease). With large interest in breast cancer predisposition testing, misinterpretation is particularly worrisome. People who already have breast cancer are asking the clinical question: "is my disease caused by a heritable genetic mutation?" The relatives of the those with breast cancer are asking the question: "Am I also a carrier of the mutation my relative has? Thus, is my risk increased, and should I undergo a more aggressive surveillance program."

SUMMARY OF THE INVENTION

The present invention is based on the isolation of a coding sequence of the BRCA1 gene found in human individuals.

It is an object of the invention to define a haplotype of a BRCA1 gene, BRCA1(omi4), in normal individuals which does not correspond to increased cancer susceptibility.

It is another object of this invention to sequence a BRCA1 gene or portion thereof and compare it to the newly discovered haplotype, BRCA1(omi4), to determine whether a sequence variation noted represents a polymorphism or a potentially harmful mutation.

It is another object of the invention to provide a protein sequence coded for by the coding sequence of the BRCA1 gene.

It is another object of the invention to provide a list of the codon pairs which occur at each of seven polymorphic points on the BRCA1 gene.

It is another object of the invention to provide a method wherein the BRCA1 gene, or parts thereof, are amplified with one or more oligonucleotide primers.

It is another object of this invention to provide a method of identifying individuals who carry no mutation(s) of the BRCA1 coding sequence and therefore have no increased genetic susceptibility to breast or ovarian cancer based on their BRCA1 genes.

It is another object of this invention to provide a method of identifying a mutation leading to an increased genetic susceptibility to breast or ovarian cancer.

It is another object of the invention to encompass prokaryotic or eukaryotic host cells comprising an expression vector having a DNA sequence that encodes for all or a fragment of the BRCA1(omi4) protein, a BRCA1(omi4) polypeptide, or a functional equivalent thereof.

It is another object of the invention to encompass all or fragments of BRCA1(omi4) protein, BRCA1(omi4) polypeptides, and functional equivalents thereof.

It is another object of the invention to encompass an anti-BRCA1(omi4) protein antibody or an antibody using a BRCA1(omi4) polypeptide or a functional equivalent thereof as an immunogen.

There is a need in the art for sequences of the BRCA1 gene and for the protein sequences of BRCA1 from normal individuals who are not at risk for increased susceptibility for cancer. In order to determine whether a sample from a patient suspected of containing a BRCA1 mutation actually has the mutation, the patient's BRCA1 DNA and/or amino acid sequence need to be compared to all known normal BRCA1 sequences. Failure to compare the sequence obtained to all naturally occurring normal sequences may result in reporting a sample as containing a potentially harmful mutation when it is a polymorphism without clinical significance.

A person skilled in the art of genetic susceptibility testing will find the present invention useful for:

a) identifying individuals having a BRCA1 gene with no coding mutations, who therefore cannot be said to have an increased genetic susceptibility to breast or ovarian cancer from their BRCA1 genes;

b) avoiding misinterpretation of polymorphisms found in the BRCA1 gene;

c) determining the presence of a previously unknown mutation in the BRCA1 gene.

d) identifying a mutation which increases the genetic susceptibility to breast or ovarian cancer.

e) probing a human sample of the BRCA1 gene by allele to determine the presence or absence of either polymorphic allels or mutations;

f) performing gene therapy with the BRCA1(omi4) gene sequence or parts thereof;

g) performing protein replacement therapy with the BRCA1(omi4) protein sequence or a functional equivalent thereof; and (h) performing diagnosis with a reagent derived from the BRCA1(omi4) DNA and protein sequence.

DETAILED DESCRIPTION OF THE INVENTION

Definitions

The following definitions are provided for the purpose of understanding this invention.

"Breast and Ovarian cancer" is understood by those skilled in the art to include breast and ovarian cancer in women and also breast and prostate cancer in men. BRCA1 is also associated with genetic susceptibility to colon cancer. Therefore, claims in this document which recite breast and/or ovarian cancer refer to breast, ovarian, prostate, and colon cancers in men and women.

"Coding sequence" or "DNA coding sequence" refers to those portions of a gene which, taken together, code for a peptide (protein), or which nucleic acid itself has function.

"Protein" or "peptide" refers to a sequence of amino acids which has function.

"BRCA1(omi4)" refers to the BRCA1(omi4) coding sequences. The BRCA1(omi4) gene refers to the gene encoding the coding sequence and its introns (particularly the splice sites adjacent to the exons) and regulatory sequences. In the present invention, the gene or its fragments are generally isolated from the host cells and in a non-chromosomal form.

"BRCA1(omi4)" refers to SEQ ID NO:1, a coding sequence for the BRCA1 gene. The coding sequence was found by end to end sequencing of a BRCA1 allele from an individual. The sequenced gene was found not to contain any mutations. BRCA1(omi4) defines a new haplotype. This sequence variation is believed to be an allele whose haplotype does not indicate an increased risk for cancer.

"Primer" as used herein refers to an oligonucleotide comprising about 20 or more nucleotides having a sequence complementary to the BRCA1 gene. Other primers which can be used for primer hybridization will be known or readily ascertainable to those of skill in the art.

"Genetic susceptibility" refers to the susceptibility to breast or ovarian cancer due to the presence of a mutation in the BRCA1 gene.

"Target polynucleotide" refers to the nucleic acid sequence of interest e.g., the BRCA1 encoding polynucleotide.

"Coding sequence" or "DNA coding sequence" refers to those portions of a gene which, taken together, code for a peptide (protein), or for which the nucleic acid itself has function.

"Consensus" means the most commonly occurring in the population.

"Consensus genomic sequence" means the allele of the target gene which occurs with the greatest frequency in a population of individuals having no family history of disease associated with the target gene.

"Substantially complementary to" refers to a probe or primer sequences which hybridize to the sequences provided under stringent conditions and/or sequences having sufficient homology with BRCA1 sequences, such that the allele specific oligonucleotide probe or primers hybridize to the BRCA1 sequences to which they are complimentary.

"Haplotype" refers to a series of specific alleles within a gene along a chromosome.

"Isolated" as used herein refers to substantially free of other poly or oligonucleic acids, proteins, lipids, carbohydrates or other materials with which they may be associated. Such association is typically either in cellular material or in a synthesis medium.

"Mutation" refers to a base change or a gain or loss of base pair(s) in a DNA sequence, which results in a DNA sequence which codes for a non-functioning protein or a protein with substantially reduced or altered function.

"Polymorphism" refers to a base change in a DNA sequence which is not associated with known pathology.

"Biological sample" refers to a polynucleotide containing sample originally from a biological source. The sample may be from a living, dead or even archeological source from a variety of tissues and cells. Examples include: body fluid [blood (leukocytes), urine (epithelial cells), saliva, breast milk, menstrual flow, cervical and vaginal secretions, etc.] skin, hair roots/follicle, mucus membrane (e.g. buccal or tongue cell scrapings), cervicovaginal cells (from PAP smear, etc.), lymphatic tissue, internal tissue (normal or tumor).

"Vector" refers to any polynucleotide which is capable of self replication or inducing integration into a self replicating polynucleotide. Examples include polynucleotides containing an origin or replication or an integration site. Vectors may be intergrated into the host cell's chromosome or form an autonomously replicating unit.

"A BRCA1 tumor growth inhibitor" refers to a molecule such as, the BRCA1(omi4) protein, a homologous polypeptide, or a functional equivalent thereof that is effective for preventing the formation of, reducing or eliminating a transformed or malignant phenotype of breast or ovarian cancer cells.

"A BRCA1(omi4) polypeptide" refers to a BRCA1 polypeptide either directly derived from the BRCA1(omi4) protein, or homologous to the BRCA1(omi4) protein, or a fusion protein thereof.

"A functional equivalent" refers to a molecule including an unnatural BRCA1(omi4) polypepide, a drug, or a natural product which retains substantial biological activity as the native BRCA1(omi4) protein in preventing, diagnosing, monitoring, and treating breast and ovarian cancer.

The invention in several of its embodiments includes: an isolated DNA sequence of the BRCA1 coding sequence as set forth in SEQ ID NO:1, a protein sequence of the BRCA1 protein as set forth in SEQ ID NO:2, a method of identifying individuals having a mutant or normal BRCA1 gene, a method of detecting an increased genetic susceptibility to breast and ovarian cancer in an individual resulting from the presence of a mutation in the BRCA1 coding sequence, a method of performing gene therapy to prevent or treat a tumor, and a method of protein replacement therapy to prevent or treat a tumor.

While a different BRCA1 haplotype which appears to encode for the same amino acid sequence has very recently been published (Shattuck-Eidens et al., *J. Am. Med. Assn.* 278(15) 1242–1250 (1997)), applicants have determined the complete nucleotide and amino acid sequence for BRCA1 (omi4) as defined in SEQ ID NO:1 and SEQ ID NO:2 and reduced the invention to practice before this publication date.

The BRCA1(omi4) haplotype is described as encompassing the alternative alleles found at polymorphic nucleotide sites 2201, 2430, 2731, 3232, 3667, 4427, and 4956. For comparison, the haplotype that is GENBANK #Accession Number U14680 is designated as haplotype #1 in TABLE I. The haplotype of U.S. Pat. No. 5,654,155, is designated as haplotype #2. Other published variations at these seven nucleotide sites are also provided. It should be noted that it has been published (Shattuck-Eidens et al., *J. Am. Med. Assn.* 278(15) 1242–1250 (1997)) that the polymorphism occurs at 3233 rather than 3232. This difference appears to be the result of an equipment error or the number accorded to the sequence as when the sequencing is performed by experienced technologists and manually interpretated independently, the polymorphism occurs at nucleotide position 3232.

TABLE I

| nucleotide position | #1 | #2 | #3 | #4 | #5 | #6 | omi4 |
|---|---|---|---|---|---|---|---|
| 2201 | C | T | C | C | T | C | T |
| 2430 | T | C | T | T | T | T | C |
| 2731 | C | T | C | T | T | C | T |
| 3232 | A | G | A | A | A | G | A |
| 3667 | A | G | A | A | G | A | G |
| 4427 | T | C | C | T | T | C | C |
| 4956 | A | G | G | A | G | G | G |

Sequencing

Any nucleic acid specimen, in purified or non-purified form, can be utilized as the starting nucleic acid, providing it contains, or is suspected of containing, the specific nucleic acid sequence containing a polymorphic locus. Thus, the process may amplify, for example, DNA or RNA, including messenger RNA and cDNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous method, such as an amplification reaction using the same or different primers may be so utilized. See the BIC for representative primers which may be used for PCR amplification. The specific nucleic acid sequence to be amplified, i.e., the polymorphic locus, may be a fraction of a larger molecule or can be present initially as a discrete molecule, so that the specific sequence constitutes the entire nucleic acid. A variety of amplification techniques may be used such as ligating the DNA sample or fragments thereof to a vector capable of replication or incorporation into a replicating system thereby increasing the number of copies of DNA suspected of containing at least a portion of the BRCA1 gene. Amplification techniques include so called "shot gun cloning." It is not necessary that the sequence to be amplified be present initially in a pure form; it may be a minor fraction of a complex mixture, such as contained in whole human DNA.

It should be noted that one need not sequence the entire coding region or even an entire DNA fragment in order to determine whether or not a mutation is present. For example, when a mutation is known in one family member, it is sufficient to determine the sequence at only the mutation'site by sequencing or by other mutation detection system, such as allele-specific oligonucleotide (ASO), when testing other family members.

DNA utilized herein may be extracted from a body sample, such as blood, tissue material and other biological samples by a variety of techniques such as that described by Maniatis, et. al. *Molecular Cloning: A Laboratory Manual*, Cold Spring Harbor, N.Y., p. 280–281, (1982). If the extracted sample is impure, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

For amplification by cloning, the DNA containing sample may be cleaved into fragments by a restriction endonuclease or by shearing by passing the DNA containing mixture through a 25 gauge needle from a syringe to prepare 1–1.5 kb fragments. The fragments are then ligated to a cleaved vector, (virus, plasmid, transposon, cosmid etc.) and then the recombinant vector so formed is then replicated in a manner typical for that vector.

For a PCR amplification, the deoxyribonucleotide triphosphates DATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to a temperature which is preferable for primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. When using thermostable DNA polymerase such as Taq, higher temperatures may be used.

The primers used to carry out this invention embrace oligonucleotides of sufficient length and appropriate sequence to provide initiation of DNA polymerization. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers used to carry out this invention are designed to be substantially complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' sequences flanking the mutation to hybridize therewith and permit amplification of the genomic locus.

Oligonucleotide primers of the invention are employed in the amplification process which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymerase I (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al., *Tetrahedron Letters,* 22:1859–1862, 1981. One method for synthesizing oligonucleotides on a modified solid support is described in U.S. Pat. No. 4,458,066.

The "agent for polymerization" may be any compound or system which will function to accomplish the synthesis of primer extension products, including enzymes. Suitable enzymes for this purpose include, for example, *E. coli* DNA polymerase I, Klenow fragment of *E. coli* DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. Suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion. Amplification is described in *PCR. A Practical Approach,* ILR Press, Eds. M. J. McPherson, P. Quirke, and G. R. Taylor, 1992.

The amplification products may be detected by Southern blots analysis, without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Indirect labeling may be performed by binding a ligand or receptor to the probe, primer or amplified product and then contacting it with a labeled corresponding receptor or ligand. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et. al., *Bio/Technology,* 3:1008–1012, 1985), allele-specific oligonucleotide (ASO) probe analysis (Conner, et. al., *Proc. Natl. Acad. Sci. U.S.A.*, 80:278, 1983), oligonucleotide ligation assays (OLAs) (Landgren, et. al., *Science*, 241:1007, 1988), RFLP and the like. Molecular techniques for DNA analysis have been reviewed (Landgren, et. al., *Science*, 242:229–237, 1988).

Preferably, the method of amplifying is by PCR, as described herein and as is commonly used by those of ordinary skill in the art. Alternative methods of amplification have been described and can also be employed as long as the BRCA1 locus amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ fold. Another amplification system useful in the method of the invention is the Qβ Replicase System. The Qβ replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking DNA repair. Nucleic acid amplification by strand displacement activation (SDA) utilizes a short primer containing a recognition site for Hinc II with short overhang on the 5' end which binds to target DNA. A DNA polymerase fills in the part of the primer opposite the overhang with sulfur-containing adenine analogs. Hinc II is added but only cuts the unmodified DNA strand. A DNA polymerase that lacks 5' exonuclease activity enters at the cite of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented Temperature cycling.

Another method is a process for amplifying nucleic acid sequences from a DNA or RNA template which may be purified or may exist in a mixture of nucleic acids. The resulting nucleic acid sequences may be exact copies of the template, or may be modified. The process has advantages over PCR in that it increases the fidelity of copying a specific nucleic acid sequence, and it allows one to more efficiently detect a particular point mutation in a single assay. A target nucleic acid is amplified enzymatically while avoiding strand displacement. Three primers are used. A first primer is complementary to the first end of the target. A second primer is complementary to the second end of the target. A third primer which is similar to the first end of the target and which is substantially complementary to at least a portion of the first primer such that when the third primer is hybridized to the first primer, the position of the third primer complementary to the base at the 5' end of the first primer contains a modification which substantially avoids strand displacement. This method is detailed in U.S. Pat. No. 5,593,840 to Bhatnagar et al. 1997.

Finally, recent application of DNA chips or microarray technology where DNA or oligonucleotides are immobilized on small solid support may also be used to rapidly sequence sample gene and analyze its expression. Typically, high density arrays of DNA fragment are fabricated on glass or nylon substrates by in situ light-directed combinatorial synthesis or by conventional synthesis followed by immobilization (U.S. Pat. No. 5,445,934). Sample DNA or RNA may be amplified by PCR, labeled with a fluorescent tag, and hybridized to the microarray. Examples of this technology are provided in U.S. Pat. Nos. 5,510, 270 and 5,547,839, incorporated herein by reference.

The BRCA1(omi4) DNA coding sequence was obtained by end to end sequencing of the BRCA1 alleles of a subject in the manner described above followed by analysis of the data obtained. The data obtained provided a previously unpublished polymorphism.

Gene Therapy

The coding sequences can be used for gene therapy. A variety of methods are known for gene transfer, any of which might be available for use.

Direct injection of Recombinant DNA in vivo:
1. Direct injection of "naked" DNA directly with a syringe and needle into a specific tissue, infused through a vascular bed, or transferred through a catheter into endothelial cells.
2. Direct injection of DNA that is contained in artificially generated lipid vesicles, or other suitable encapsulating vehicle.
3. Direct injection of DNA conjugated to a target receptor structure, such as a diptheria toxin, an antibody, or other suitable receptor.
4. Direct injection by particle bombardment, where the DNA is coated onto gold particles and shot into the cells.

Human Artificial Chromosomes

This gene delivery approach involves the use of human chromosomes that have been stripped down to contain only the essential components for replication and the genes desired for transfer.

Receptor-Mediates Gene Transfer

DNA is linked to a targeting molecule that will bind to specific cell-surface receptors, inducing endocytosis and transfer of the DNA into mammalian cells. One such technique uses poly-L-lysine to link asialoglycoprotein to DNA. An adenovirus is also added to the complex to disrupt the lysosomes and thus allow the DNA to avoid degradation and move to the nucleus. Infusion of these particles intravenously has resulted in gene transfer into hepatocytes.

Recombinant Virus Vectors

Several vectors are used in gene therapy. Among them are the Moloney Murine Leukemia Virus (MoMLV) Vectors, the adenovirus vectors, the Adeno-Associated Virus (AAV) vectors, the retrovirus vectors, the herpes simplex virus (HSV) vectors, the poxvirus vectors, and human immunodeficiency virus (HIV) vectors.

Gene Replacement and Repair

The ideal genetic manipulation for treatment of a genetic disease would be the actual replacement of the defective gene with a normal copy of the gene. Homologous recombination is the term used for switching out a section of DNA and replacing it with a new piece. By this technique, the defective gene can be replaced with a normal gene which expresses a functioning BRCA1 tumor growth inhibitor protein.

A complete description of gene therapy can also be found in "Gene Therapy A Primer For Physicians" 2d Ed. by Kenneth W. Culver, M.D. Publ. Mary Ann Liebert Inc. (1996). Two Gene Therapy Protocols for BRCA1 are approved by the Recombinant DNA Advisory Committee for Jeffrey T. Holt et al. They are listed as 9602-148, and 9603-149 and are available from the NIH. The isolated BRCA1 gene can be synthesized or constructed from amplification products and inserted into a vector such as the LXSN vector. Triple strand gene repair may also be used. See U.S. Pat. Nos. 5,650,316 and 5,624,803, for example.

A BRCA1(OMI4) Polypeptide or its Functional Equivalent

It has been shown that active BRCA1 protein inhibits the growth of the cancer cells and reduces tumorigenesis. Thus, the growth of breast or ovarian cancer may be arrested or prevented by increasing the BRCA1 protein level where inadequate functional BRCA1 activity is responsible for breast or ovarian cancer. The cDNA and amino acid sequences of the BRCA1(omi4) haplotype are disclosed herein (SEQ ID No: 1 and 2, respectively). All or a fragment of the BRCA1(omi4) protein may be used in therapeutic or prophylactic treatment of breast or ovarian cancer. Such a fragment may have a similar biological function as the native BRCA1(omi4) protein or may have a desired biological function as specified below. BRCA1(omi4) polypeptides or their functional equivalents including homologous and modified polypeptide sequences are also within the scope of the present invention. Changes in the native sequence may be advantageous in producing or using the BRCA1(omi4) derived polypeptide or functional equivalent suitable for therapeutic or prophylactic treatment of breast or ovarian cancer. For example, these changes may be desirable for producing resistance against in vivo proteolytic cleavage, for facilitating transportation and delivery of therapeutic reagents, for localizing and compartmentalizing tumor suppressing agents, or for expression, isolating and purifying the target species.

There are a variety of methods to produce an active BRCA1(omi4) polypeptide or a functional equivalent as a tumor growth inhibitor. For example, one or more amino acids may be substituted, deleted, or inserted using methods well known in the art (Maniatis et al., 1982). Considerations of polarity, charge, solubility, hydrophobicity, hydrophilicity and/or the amphiphathic nature of the amino acids play an important role in designing homologous polypeptide changes suitable for the intended treatment. In particular, conservative amino acid substitution using amino acids that are related in side-chain structure and charge may be employed to preserve the chemical and biological property. A homologous polypeptide typically contains at least 70% sequence homology to the native sequence. Unnatural forms of the polypeptide may also be incorporated so long as the modification retains substantial biological activity. These unnatural forms typically include structural mimics and chemical medications, which have similar three-dimensional structures as the active regions of the native BRCA1(omi4) protein. For example, these modifications may include terminal D-amino acids, cyclic peptides, unnatural amino acids side chains, pseudopeptide bonds, N-terminal acetylation, glycosylation, and biotinylation, etc. These unnatural forms polypeptide may have a desired biological function, for example, they be particularly robust in the presence of cellular or serum proteases and exopeptidases. An effective BRCA1(omi4) polypepitde or a functional equivalent may also be recognized by the reduction of the native BRCA1 protein. Regions of the BRCA1 protein may be systematically deleted to identify which regions are essential for tumor growth inhibitor activity. These smaller fragments of BRCA1(omi4) protein may then be subjected to structural and functional modification to derive the therapeutically or prophylactically effective regiments. Finally, drugs, natural products or small molecules may be screened or synthesized to mimic the function of the BRCA1 protein. Typically, the active species retain the essential three-dimensional shape and chemical reactivity, and therefore retain the desired aspects of the biological activity of the native BRCA1 protein. The activity and function of the BRCA1 protein may include transcriptional activation, granin, DNA repair, among others. Functions of the BRCA1 protein are also reviewed in Bertwistle and Ashworth, Curr. Opin. Genet. Dev. 8(1): 14–20 (1998) and Zhang et al., Cell 92:433–436 (1998). It will be apparent to one skilled in the art that a BRCA1(omi4) polypeptide or a functional equivalent may be selected because such polypeptide or functional equivalent possesses similar biological activity as the native BRCA1 protein.

Expression of the BRCA1(omi4) Protein and Polypeptide in Host Cells

All or fragments of the BRCA1(omi4) protein and polypeptide may be produced by host cells that are capable of directing the replication and the expression of foreign genes. Suitable host cells include prokaryotes, yeast cells, or higher eukaryotic cells, which contain an expression vector comprising all or a fragment of the BRCA1(omi4) cDNA sequence (SEQ. ID No: 1) operatively linked to one or more regulatory sequences to produce the intended BRCA1(omi4) protein or polypeptide. Prokaryotes may include gram negative or gram positive organisms, for example E. coli or Bacillus strains. Suitable eukaryotic host cells may include yeast, virus, and mamalian systems. For example, Sf9 insect cells and human cell lines, such as COS, MCF7, HeLa, 293T, HBL100, SW480, and HCT116 cells.

A broad variety of suitable expression vectors are available in the art. An expression vector typically contains an origin of replication, a promoter, a phenotypic selection gene (antibiotic resistance or autotrophic requirement), and a DNA sequence coding for all or fragments of the BRCA1 (omi4) protein. The expression vectors may also include other operatively linked regulatory DNA sequences known in the art, for example, stability leader sequences, secretory leader sequences, restriction enzyme cleavage sequences, polyadenylation sequences, and termination sequences, among others. The essential and regulatory elements of the expression vector must be compatible with the intended host cell. Suitable expression vectors containing the desired coding and control regions may be constructed using standard recombinant DNA techniques known in the art, many of which are described in Sambrook, et al., Molecular Cloning: A Laboratory Manual, Second Edition, Cold Spring Harbor Laboratory, Cold Spring Harbor, N.Y. (1989).

For example, suitable origins of replication may include Col E1, SV4O viral and M13 origins of replication. Suitable promoters may be constitutive or inducible, for example, tac promoter, lac Z promoter, SV40 promoter, MMTV promoter, and LXSN promoter. Examples of selectable markers include neomycin, ampicillin, and hygromycin resistance and the like. Many suitable prokaryotic, viral and mammalian expression vectors may be obtained commercially, for example, from Invitrogen Corp., San Diego, Calif. or from Clontech, Palo Alto, Calif. It may be desirable that the BRCA1(omi4) protein or polypeptide is produced as a fusion protein to enhance the expression in selected host cells, to detect the expression in transfected cells, or to simplify the purification process. Suitable fusion partners for the BRCA1(omi4) protein or polypeptide are well known in the art and may include β-galactosidase, glutathione-S-transferase and poly-histidine tag, among others.

Expression vectors may be introduced into host cells by various methods known in the art. The transformation procedure used depends upon the host to be transformed. Methods for introduction of vectors into host cells may include calcium phosphate precipitation, electrosporation, dextran-mediated transfection, liposome encapsulation, nucleus microinjection, and viral or phage infection, among others.

Once an expression vector has been introduced into a suitable host cell, the host cell may be cultured under conditions permitting expression of large amounts of the BRCA1(omi4) protein or polypeptide. The expression product may be identified by many approaches well known in the art, for example, sequencing after PCR-based amplification, hybridization using probes complementary to the desired DNA sequence, the presence or absence of marker gene functions such as enzyme activity or antibiotic resistance, the level of mRNA production encoding the intended sequence, immunological detection of a gene product using monoclonal and polyclonal antibodies, such as Western blotting or ELISA. The BRCA1(omi4) protein or polypeptides produced in this manner may then be isolated following cell lysis and purified using various protein purification techniques known in the art, for example, ion exchange chromatography, gel filtration chromatography and immunoaffinity chromatography.

It is generally preferred that whenever possible, longer fragments of BRCA1(omi4) protein or polypeptide are used, particularly to include the desired functional domains of BRCA1 protein. Expression of shorter fragments of DNA may be useful in generating BRCA1(omi4) derived immunogen for the production of anti-BRCA1(omi4) antibodies. It should, of course, be understood that not all expression vectors, DNA regulatory sequences or host cells will function equally well to express the BRCA1(omi4) protein or polypeptides of the present invention. However, one of ordinary skill in the art may make a selection among expression vectors, DNA regulatory sequences, host cells, and codon usage in order to optimize expression using known technology in the art without undue experimentation. Studies of the BRCA1 protein and examples of genetic manipulation of the BRCA1 protein are summarized in two recent review articles, Bertwistle and Ashworth, *Curr. Opin. Genet. Dev.* 8(1): 14–20 (1998) and Zhang et al., *Cell* 92:433–436 (1998).

In Vitro Synthesis and Chemical Synthesis

Although it is preferred that the BRCA1(omi4) protein or polypeptides be obtained by overexpression in prokaryotic or eukaryotic host cells, the BRCA1(omi4) polypeptides or their functional equivalents may also be obtained by in vitro translation or synthetic means by methods known to those of ordinary skill in the art. For example, in vitro translation may employ a mRNA encoded by a DNA sequence coding for all or fragments of the BRCA1(omi4) protein or polypeptides. Chemical synthesis methodology such as solid phase synthesis may be used to synthesize a BRCA1(omi4) polypeptide structural mimic and chemically modified analogs thereof. The polypeptides or the modifications and mimic thereof produced in this manner may then be isolated and purified using various purification techniques, such as chromatographic procedures including ion exchange chromatography, gel filtration chromatography and immunoaffinity chromatography.

Protein Replacement Therapy

The ability of the BRCA1 protein to inhibit tumor growth demonstrates that various BRCA1 protein targeted therapies may be utilized in treating and preventing tumors in breast and ovarian cancer. The present invention therefore includes therapeutic and prophylactic treatment of breast and ovarian cancer using therapeutic pharmaceutical compositions containing the BRCA1(omi4) protein, polypeptides, or their functional equivalents. For example, protein replacement therapy may involve directly administering the BRCA1 (omi4) protein, a BRCA1(omi4) polypeptide, or a functional equivalent in a pharmaceutically effective carrier. Alternatively, protein replacement therapy may utilize tumor antigen specific antibody fused to the BRCA1(omi4) protein, a polypeptide, or a functional equivalent to deliver anti-cancer regiments specifically to the tumor cells.

To prepare the pharmaceutical compositions of the present invention, an active BRCA1(omi4) protein, a polypeptide, or its functional equivalent is combined with a pharmaceutical carrier selected and prepared according to conventional pharmaceutical compounding techniques. A suitable amount of the composition may be administered locally to the site of a tumor or systemically to arrest the proliferation of tumor cells. The methods for administration may include parenteral, oral, or intravenous, among others according to established protocols in the art.

Pharmaceutically acceptable solid or liquid carriers or components which may be added to enhance or stabilize the composition, or to facilitate preparation of the composition include, without limitation, syrup, water, isotonic solution, 5% glucose in water or buffered sodium or ammonium acetate solution, oils, glycerin, alcohols, flavoring agents, preservatives, coloring agents, starches, sugars, diluents, granulating agents, lubricants, binders, and sustained release materials. The dosage at which the therapeutic compositions are administered may vary within a wide range and depends on various factors, such as the stage of cancer progression, the age and condition of the patient, and may be individually adjusted.

Diagnostic Reagents

The BRCA1(omi4) protein, polypeptides, their functional equivalents, antibodies, and polynucleotides may be used in a wide variety of ways in addition to gene therapy and protein replacement therapy. They may be useful as diagnostic reagents to measure normal or abnormal activity of BRCA1 at the DNA, RNA and protein level. The present invention therefore encompasses the diagnostic reagents derived from the BRCA1(omi4) cDNA and protein sequences as set forth in SEQ. ID. Nos: 1 and 2 respectively. These reagents may be utilized in methods for monitoring disease progression, for determining patients suited for gene and protein replacement therapy, or for detecting the presence or quantifying the amount of a tumor growth inhibitor following such therapy. Such methods may involve conventional histochemical techniques, such as obtaining a tumor tissue from the patient, preparing an extract and testing this extract for tumor growth or metabolism. For example, the test for tumor growth may involve measuring abnormal BRCA1(omi4) activity using conventional diagnostic assays, such as Southern, Northern, and Western blotting, PCR, RT-PCR, immunoassay, and immunoprecipitation. In biopsies of tumor tissues, the loss of the BRCA1(omi4) expression in tumor tissue may be verified by RT-PCR and Northern blotting at the RNA level. A Southern blot analysis, genomic PCR, or fluorescence in situ hybridization (FISH) may also be performed to examine the mutations of BRCA1 at the DNA level. And, a Western blotting, protein truncation assay, or immunoprecipitation may be utilized to analysis the effect at the protein level.

These diagnostic reagents are typically either covalently or non convalently attached to a detectable label. Such a label includes a radioactive label, a calorimetric enzyme label, a fluorescence label, or an epitope label. Frequently, a reporter gene downstream of the regulatory sequences is fused with the BRCA1(omi4) protein or polypeptide to facilitate the detection and purification of the target species. Commonly used reporter genes in BRCA1 fusion proteins include β-galactosidase and luciferase gene.

The BRCA1(omi4) protein, polypeptides, their functional equivalents, antibodies, and polynucleotides may also be useful in the study of the characteristics of the BRCA1 protein, such as structure and function of BRCA1 in oncogenesis or subcellular localization of the BRCA1 protein in normal and cancerous cells. For example, yeast two-hybrid system has been frequently used in the study of cellular function of BRCA1 to identify the regulator and effector of BRCA1 growth control pathways (See reviews of Bertwistle and Ashworth, 1998 and Zhange et al., 1998). In addition, the BRCA1(omi4) protein, polypeptides, their functional equivalents, antibodies, and polynucleotides may also be used in in vivo cell based and in vitro cell free assays to screen natural products and synthetic compounds which may mimic, regulate or stimulate BRCA1 protein function.

Antisense Inhibition

Antisense suppression of endogenous BRCA1 expression may assess the effect of the BRCA1 protein on cell growth inhibition using known method in the art (Crooke, *Annu. Rev. Pharmacol. Toxicol.* 32:329–376 (1992) and Robinson-Benion and Holt, *Methods Enzymol.* 254:363–375 (1995)). Given the cDNA sequence as set forth in SEQ ID. NO: 1, one of skill in the art can readily obtain anti-sense strand of DNA and RNA sequences to interfere with the production of the wild-type BRCA1(omi4) protein or the mutated form of BRCA1 protein. Alternatively, antisense oligonucleotide may be designed to target the control sequences of BRCA1 (omi4) gene to reduce or prevent the expression of the endogenous BRCA1(omi4) gene. Examples of using oligonucleotide-based antisense technology to inhibit the BRCA1 expression are provided in Husain et al., *Cancer Res.* 58:1120–1123 (1998).

Antibodies

The BRCA1(omi4) protein, polypeptides, or their functional equivalent may be used as immunogens to prepare polyclonal or monoclonal antibodies capable of binding the BRCA1 derived antigens in a known manner (Harlow & Lane, Antibodies: A Laboratory Manual, Cold Spring Harbor Laboratory, Cold Spring Harbor, N.Y., 1988). These antibodies may be used for the detection of the BRCA1 protein, polypeptides, or a functional equivalent in an immunoassay, such as ELISA, Western blot, radioimmunoassay, enzyme immunoassay, and immunocytochemistry. Typically, an anti-BRCA1 antibody is in solution or is attached to a solid surface such as a plate, a particle, a bead, or a tube. The antibody is allowed to contact a biological sample or a blot suspected of containing the BRCA1 protein or polypeptide to form a primary immunocomplex. After sufficient incubation period, the primary immunocomplex is washed to remove any non-specifically bound species. The amount of specifically bound BRCA1 protein or polypeptide may be determined using the detection of an attached label or a marker, such as a radioactive, a fluorescent, or an enzymatic label. Alternatively, the detection of BRCA1 derived antigen is allowed by forming a secondary immunocomplex using a second antibody which is attached with a such label or marker. The antibodies may also be used in affinity chromatography for isolating or purifying the BRCA1 protein, polypeptides or their functional equivalents. Examples of preparing and using anti-BRCA1 antibodies are provided in Ruffner et al., *Proc. Natl. Acad. Sci. USA* 94:7138–7143 (1997) and Jensen et al., *Nat. Genetics* 12:303–308 (1996).

EXAMPLE 1

Determination Of The Coding Sequence Of A BRCA1 Gene

Materials and Methods

A blood sample from an individual who may have been at risk for hereditary cancer was obtained. This sample was chosen for end-to-end sequencing of the BRCA1 gene.

Genomic DNA was isolated from the white blood cells of the sample. Dideoxy sequence analysis was performed following polymerase chain reaction amplification.

All exons of the BRCA1 gene were subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye was attached for automated sequencing using the TAQ DYE TERMINATOR® KIT (PERKIN-ELMER cat#401628). DNA sequencing was performed in both forward and reverse directions on an APPLIED BIOSYSTEMS, INC. (ABI) automated Model 377® sequencer. The software used for analysis of the resulting data was SEQUENCE NAVIGATOR® software purchased through ABI.

1. Polymerase Chain Reaction (PCR) Amplification

Genomic DNA (100 nanograms) extracted from white blood cells of the blood sample. The BRCA1 gene was sequenced end to end. The sample was amplified in a final volume of 25 microliters containing 1 microliter (100 nanograms) genomic DNA, 2.5 microliters 10×PCR buffer (100 mM Tris, pH 8.3, 500 mM KCl, 1.2 mM $MgCl_2$), 2.5 microliters 10×DNTP mix (2 mM each nucleotide), 2.5 microliters forward primer, 2.5 microliters reverse primer, and 1 microliter Taq polymerase (5 units), and 13 microliters of water.

The primers in Table IV, below were used to carry out amplification of the various sections of the BRCA1 gene samples. The primers were synthesized on an DNA/RNA MODEL 394® SYNTHESIZER.

TABLE IV

BRCA1 PRIMERS AND SEQUENCING DATA

| EXON | SEQUENCE | SEQ ID NO: | MER | Mg++ | SIZE |
|---|---|---|---|---|---|
| 2-2F | 5'GAA GTT GTC ATT TTA TAA ACC TTT-3' | 3 | 24 | 1.6 | ~275 |
| 2R | 5'TGT CTT TTC TTC CCT AGT ATG T-3' | 4 | 22 | | |
| 3-3F | 5'TCC TGA CAC AGC AGA CAT TTA-3' | 5 | 21 | 1.4 | ~375 |
| 3R | 5'TTG GAT TTT CGT TCT CAC TTA-3' | 6 | 21 | | |
| 5-5F | 5'CTC TTA AGG GCA GTT GTG AG-3' | 7 | 20 | 1.2 | ~275 |
| 5R | 5'TTC CTA CTG TGG TTG CTT CC-3' | 8 | 20 | | |
| 6-6/7F | 5'CTT ATT TTA GTG TCC TTA AAA GG-3' | 9 | 23 | 1.6 | ~250 |
| 6R | 5'TTT CAT GGA CAG CAC TTG AGT G-3' | 10 | 22 | | |
| 7-7F | 5'CAC AAC AAA GAG CAT ACA TAG GG-3' | 11 | 23 | 1.6 | ~275 |
| 6/7R | 5'TCG GGT TCA CTC TGT AGA AG-3' | 12 | 20 | | |
| 8-8F1 | 5'TTC TCT TCA GGA GGA AAA GCA-3' | 13 | 21 | 1.2 | ~270 |
| 8R1 | 5'GCT GCC TAC CAC AAA TAC AAA-3' | 14 | 21 | | |
| 9-9F | 5'CCA CAG TAG ATG CTC AGT AAA TA-3' | 15 | 23 | 1.2 | ~250 |
| 9R | 5'TAG GAA AAT ACC AGC TTC ATA GA-3' | 16 | 23 | | |
| 10-10F | 5'TGG TCA GCT TTC TGT AAT CG-3' | 17 | 20 | 1.6 | ~250 |
| 10R | 5'GTA TCT ACC CAC TCT CTT CAG-3' | 18 | 24 | | |
| 11A11AF | 5'CCA CCT CCA AGG TGT ATC A-3' | 19 | 19 | 1.2 | 372 |
| 11AR | 5'TGT TAT GTT GGC TCC TTG CT-3' | 20 | 20 | | |
| 11B11BF1 | 5'CAC TAA AGA CAG AAT GAA TCT A-3' | 21 | 21 | 1.2 | ~400 |
| 11BR1 | 5'GAA GAA CCA GAA TAT TCA TCT A-3' | 22 | 21 | | |
| 11C-11CF1 | 5'TGA TGG GGA GTC TGA ATC AA-3' | 23 | 20 | 1.2 | ~400 |
| 11CR1 | 5'TCT GCT TTC TTG ATA AAA TCC T-3' | 24 | 22 | | |
| 11D-11DF1 | 5'AGC GTC CCC TCA CAA ATA AA-3' | 25 | 20 | 1.2 | ~400 |
| 11DR1 | 5'TCA AGC GCA TGA ATA TGC CT-3' | 26 | 20 | | |
| 11E-11EF | 5'GTA TAA GCA ATA TGG AAC TCG A-3' | 27 | 22 | 1.2 | 388 |
| 11ER | 5'TTA AGT TCA CTG GTA TTT GAA CA-3' | 28 | 23 | | |
| 11F-11FF | 5'GAC AGC GAT ACT TTC CCA GA-3' | 29 | 20 | 1.2 | 382 |
| 11FR | 5'TGG AAC AAC CAT GAA TTA GTC-3' | 30 | 21 | | |
| 11G-11GF | 5'GGA AGT TAG CAC TCT AGG GA-3' | 31 | 20 | 1.2 | 423 |
| 11GR | 5'GCA GTG ATA TTA ACT GTC TGT A-3' | 32 | 22 | | |
| 11H-11HF | 5'TGG GTC CTT AAA GAA ACA AAG T-3' | 33 | 22 | 1.2 | 366 |
| 11HR | 5'TCA GGT GAC ATT GAA TCT TCC-3' | 34 | 21 | | |
| 11I-11IF | 5'CCA CTT TTT CCC ATC AAG TCA-3' | 35 | 21 | 1.2 | 377 |
| 11IR | 5'TCA GGA TGC TTA CAA TTA CTT C-3' | 36 | 21 | | |
| 11J-11JF | 5'CAA AAT TGA ATG CTA TGC TTA GA-3' | 37 | 23 | 1.2 | 377 |
| 11JR | 5'TCG GTA ACC CTG AGC CAA AT-3' | 38 | 20 | | |
| 11K-11KF | 5'GCA AAA GCG TCC AGA AAG GA-3' | 39 | 20 | 1.2 | 396 |
| 11KR-1 | 5'TAT TTG CAG TCA AGT CTT CCA A-3' | 40 | 22 | | |

TABLE IV-continued

BRCA1 PRIMERS AND SEQUENCING DATA

| EXON | SEQUENCE | SEQ ID NO: | MER | Mg$^{++}$ | SIZE |
|---|---|---|---|---|---|
| 11L-11LF-1 | 5'GTA ATA TTG GCA AAG GCA TCT-3' | 41 | 22 | 1.2 | 360 |
| 11LR | 5'TAA AAT GTG CTC CCC AAA AGC A-3' | 42 | 22 | | |
| 12-12F | 5'GTC CTG CCA ATG AGA AGA AA-3' | 43 | 20 | 1.2 | ~300 |
| 12R | 5'TGT CAG CAA ACC TAA GAA TGT-3' | 44 | 21 | | |
| 13-13F | 5'AAT GGA AAG CTT CTC AAA GTA-3' | 45 | 21 | 1.2 | ~325 |
| 13R | 5'ATG TTG GAG CTA GGT CCT TAC-3' | 46 | 21 | | |
| 14-14F | 5'CTA ACC TGA ATT ATC ACT ATC A-3' | 47 | 22 | 1.2 | ~310 |
| 14R | 5'GTG TAT AAA TGC CTG TAT GCA-3' | 48 | 21 | | |
| 15-15F | 5'TGG CTG CCC AGG AAG TAT G-3' | 49 | 19 | 1.2 | ~375 |
| 15R | 5'AAC CAG AAT ATC TTT ATG TAG GA-3' | 50 | 23 | | |
| 16-16F | 5'AAT TCT TAA CAG AGA CCA GAA C-3' | 51 | 22 | 1.6 | -550 |
| 16R | 5'AAA ACT CTT TCC AGA ATG TTG T-3' | 52 | 22 | | |
| 17-17F | 5'GTG TAG AAC GTG CAG GAT TG-3' | 53 | 20 | 1.2 | ~275 |
| 17R | 5'TCG CCT CAT GTG GTT TTA-3' | 54 | 18 | | |
| 18-18F | 5'GGC TCT TTA GCT TCT TAG GAC-3' | 55 | 21 | 1.2 | ~350 |
| 18R | 5'GAG ACC ATT TTC CCA GCA TC-3' | 56 | 20 | | |
| 19-19F | 5'CTG TCA TTC TTC CTG TGC TC-3' | 57 | 20 | 1.2 | ~250 |
| 19R | 5'CAT TGT TAA GGA AAG TGG TGC-3' | 58 | 21 | | |
| 20-20F | 5'ATA TGA CGT GTC TGC TCC AC-3' | 59 | 20 | 1.2 | ~425 |
| 20R | 5'GGG AAT CCA AAT TAC ACA GC-3' | 60 | 20 | | |
| 21-21F | 5'AAG CTC TTC TTT GAA AGT C-3' | 61 | 22 | 1.6 | ~300 |
| 21R | 5'GTA GAG AAA TAG AAT AGC CTC T-3' | 62 | 22 | | |
| 22-22F | 5'TCC CAT TGA GAG GTC TTG CT-3' | 63 | 20 | 1.6 | ~300 |
| 22R | 5'GAG AAG ACT TCT GAG GCT AC-3' | 64 | 20 | | |
| 23-23F | 5'TGA AGT GAC AGT TCC AGT AGT-3' | 65 | 21 | 1.2 | ~250 |
| 23R-1 | 5'CAT TTT AGC CAT TCA TTC AAC AA-3' | 66 | 23 | | |
| 24-24F | 5'ATG AAT TGA CAC TAA TCT CTG C-3' | 67 | 22 | 1.4 | ~285 |
| 24R | 5'GTA GCC AGG ACA GTA GAA GGA-3' | 68 | 21 | | |

Thirty-five cycles were performed, each consisting of denaturing (95° C.; 30 seconds), annealing (55° C.; 1 minute), and extension (72° C.; 90 seconds), except during the first cycle in which the denaturing time was increased to 5 minutes, and during the last cycle in which the extension time was increased to 5 minutes.

PCR products were purified using QIA-QUICK® PCR purification kits (QIAGEN cat#28104; Chatsworth, Calif.). Yield and purity of the PCR product determined spectrophotometrically at OD$_{260}$ on a BECKMAN DU 650 SPECTROPHOTOMETER.

2. Dideoxy Sequence Analysis

Fluorescent dye was attached to PCR products for automated sequencing using the TAQ DYE TERMINATOR® KIT (PERKIN-ELMER cat#401628). DNA sequencing was performed in both forward and reverse directions on an APPLIED BIOSYSTEMS, INC. (ABI) Foster City, Calif., automated MODEL 377® SEQUENCER. The software used for analysis of the resulting data was "SEQUENCE NAVIGATOR® software" purchased through ABI.

3. Results

Differences in the nucleic acids of the alleles from the test individual and the known standard sequences (U.S. Pat. No. 5,654,155 and GENBANK accession number U14680 were found in seven locations on the gene. The changes and their nucleotide positions are found on TABLE I, above. The data show the BRCA1 gene of the present invention is identical except in the region of seven polymorphisms. These polymorphic regions, the amino acid groups of each codon, and the amino acid coded for by each codon are found in TABLE V below with the sequences and amino acids of the present invention given last.

an APPLIED BIOSYSTEMS, INC. (ABI) AUTOMATED MODEL 377® SEQUENCER. The software used for analysis of the resulting data is "SEQUENCE NAVIGATOR® software" purchased through ABI.

TABLE V

CODON AND NUCLEOTIDE CHANGES IN SEVEN POLYMORPHIC SITES OF THE BRCA1 GENE

| NUCLEOTIDE POSITION/ CODON | CODON U12680 | CODON 5,654,155 | CODON OMI4 | AMINO ACID U12680 | AMINO ACID 5,654,155 | AMINO ACID OMI4 |
|---|---|---|---|---|---|---|
| 2201/694 | AGC | AGT | AGT | SER | SER | SER |
| 2430/771 | TGG | CTG | CTG | LEU | LEU | LEU |
| 2731/871 | CCG | CTG | CTG | PRO | LEU | LEU |
| 3232/1038 | GAA | GGA | GAA | GLU | GLY | GLU |
| 3667/1183 | AAA | AGA | AGA | LYS | ARG | ARG |
| 4427/1436 | TCT | TCC | TCC | SER | SER | SER |
| 4956/1613 | AGT | GGT | GGT | SER | GLY | GLY |

The presence of haplotype BRCA1(omi4) was confirmed on a second DNA sample by sequencing of the pertinent regions about one month after the first sequencing of the first DNA sample.

EXAMPLE 2

Determining the Absence of a Mutation in the BRCA1 Gene Using BRCA1(omi4)for Reference A person skilled in the art of genetic susceptibility testing will find the present invention useful for:

a) identifying individuals having a BRCA1 gene, who are therefore have no elevated genetic susceptibility to breast or ovarian cancer from a BRCA1 mutation;

b) avoiding misinterpretation of polymorphisms found in the BRCA1 gene when determining the presence of a known or previously unknown mutation in the BRCA1 gene. A list of mutations of BRCA1 is publicly available in the Breast Cancer Information Core at: www.nchgr.nih.gov/dir/lab_transfer/bic. This data site became publicly available on Nov. 1, 1995. Friend, et al. *Nature Genetics*, 11:238, (1995).

Sequencing is carried out as in EXAMPLE 1 using a blood sample from the patient in question. However, a BRCA1(omi4) sequence is used for reference and polymorphic sites are compared to the nucleic acid sequences listed above for codons at each polymorphic site. A sample sequence is compared to the BRCA1(omi4) SEQ ID NO:1 sequence at each of the polymorphic sites.

All exons of the BRCA1 gene are subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye is attached for automated sequencing using the TAQ DYE TERMINATOR® KIT (PERKIN-ELMER cat#401628). DNA sequencing is performed in both forward and reverse directions on 1. Polymerase Chain Reaction (PCR) Amplification Genomic DNA (100 nanograms) extracted from white blood cells of the subject is amplified in a final volume of 25 microliters containing 1 microliter (100 nanograms) genomic DNA, 2.5 microliters 10×PCR buffer (100 mM Tris, pH 8.3, 500 mM KCl, 1.2 mM $MgCl_2$), 2.5 microliters 10×DNTP mix (2 mM each nucleotide), 2.5 microliters forward primer (10 micromolar solution), 2.5 microliters reverse primer (10 micromolar solution),and 1 microliter Taq polymerase (5 units), and 13 microliters of water.

The PCR primers used to amplify a patient's sample BRCA1 gene are listed in Table IV. The primers were synthesized on an DNA/RNA MODEL 394® SYNTHESIZER. Thirty-five cycles are of amplification are performed, each consisting of denaturing (95° C.; 30 seconds), annealing (55° C.; 1 minute), and extension (72° C.; 90 seconds), except during the first cycle in which the denaturing time is increased to 5 minutes, and during the last cycle in which the extension time is increased to 5 minutes.

PCR products are purified using QIA-QUICK® PCR PURIFICATION KITS (QIAGEN, cat#28104; Chatsworth, Calif.). Yield and purity of the PCR product determined spectrophotometrically at $OD_{260}$ on a BECKMAN DU 650 SPECTROPHOTOMETER.

2. Dideoxy Sequence Analysis

Fluorescent dye is attaches to PCR products for automated sequencing using the TAQ DYE TERMINATOR® KIT (PERKIN-ELMER cat#401628). DNA sequencing is performed in both forward and reverse directions on an APPLIED BIOSYSTEMS, INC. (ABI) Foster City, Calif., AUTOMATED MODEL 377® SEQUENCER. The software used for analysis of the resulting data is "SEQUENCE NAVIGATOR® software" purchased through ABI. The BRCA1(omi4) SEQ ID NO:1 sequence is entered into the SEQUENCE NAVIGATOR® software as the Standard for comparison. The SEQUENCE NAVIGATOR® software compares the sample sequence to the BRCA1(omi4) SEQ ID NO:1 standard, base by base. The Sequence Navigator® software highlights all differences between the BRCA1 (omi4) SEQ ID NO:1 DNA sequence and the patient's sample sequence.

A first technologist checks the computerized results by comparing visually the BRCA1(omi4) SEQ ID NO:1 standard against the patient's sample, and again highlights any differences between the standard and the sample. The first primary technologist then interprets the sequence variations at each position along the sequence. Chromatograms from each sequence variation are generated by the SEQUENCE NAVIGATOR® software and printed on a color printer. The peaks are interpreted by the first primary technologist and also by a second primary technologist. A secondary technologist then reviews the chromatograms. The results are finally interpreted by a geneticist. In each instance, a variation is compared to known polymorphisms for position and base change. If the sample BRCA1 sequence matches the BRCA1(omi4) SEQ ID NO:1 standard, with only variations within the known list of polymorphisms, it is interpreted as a gene sequence.

EXAMPLE 3

Determining the Presence of a Mutation in the BRCA1 Gene Using BRCA1(omi4) for Reference A person skilled in the art of genetic susceptibility testing will find the present invention useful for determining the presence of a known or previously unknown mutation in the BRCA1 gene. A list of mutations of BRCA1 is publicly available in the Breast Cancer Information Core at: www.nchgr.nih.gov/dir/lab_transfer/bic. This data site became publicly available on Nov. 1, 1995. Friend, et al. *Nature Genetics*, 11:238, (1995). In this example, a mutation in exon 11 is characterized by amplifying the region of the mutation with a primer which matches the region of the mutation.

Sequencing is carried out as in EXAMPLE 1 using a blood sample from the patient in question. However, a BRCA1(omi4) sequence is used for reference and polymorphic sites are compared to the nucleic acid sequences listed above for codons at each polymorphic site. A sample sequence is compared to the BRCA1(omi4) SEQ ID NO:1 sequence at each of the polymorphic sites.

All exons of the BRCA1 gene are subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye is attached for automated sequencing using the TAQ DYE TERMINATOR® KIT (PERKIN-ELMER cat#401628). DNA sequencing is performed in both forward and reverse directions on an APPLIED BIOSYSTEMS, INC. (ABI) AUTOMATED MODEL 377® SEQUENCER. The software used for analysis of the resulting data is "SEQUENCE NAVIGATOR® software" purchased through ABI.

1. Polymerase Chain Reaction (PCR) Amplification

Genomic DNA (100 nanograms) extracted from white blood cells of the subject is amplified in a final volume of 25 microliters containing 1 microliter (100 nanograms) genomic DNA, 2.5 microliters 10×PCR buffer (100 mM Tris, pH 8.3, 500 mM KCl, 1.2 mM MgCl$_2$), 2.5 microliters 10×DNTP mix (2 mM each nucleotide), 2.5 microliters forward primer (10 micromolar solution), 2.5 microliters reverse primer (10 micromolar solution),and 1 microliter Taq polymerase (5 units), and 13 microliters of water.

The primers are synthesized on an DNA/RNA MODEL 394® SYNTHESIZER. Thirty-five cycles are performed, each consisting of denaturing (95° C.; 30 seconds), annealing (55° C.; 1 minute), and extension (72° C.; 90 seconds), except during the first cycle in which the denaturing time is increased to 5 minutes, and during the last cycle in which the extension time is increased to 5 minutes.

PCR products are purified using QIA-QUICK® PCR PURIFICATION KITS (QIAGEN, cat#28104; Chatsworth, Calif.). Yield and purity of the PCR product determined spectrophotometrically at OD$_{260}$ on a BECKMAN DU 650 SPECTROPHOTOMETER.

2. Dideoxy Sequence Analysis

Fluorescent dye is attached to PCR products for automated sequencing using the TAQ DYE TERMINATOR® KIT (PERKIN-ELMER cat#401628). DNA sequencing is performed in both forward and reverse directions on an APPLIED BIOSYSTEMS, INC. (ABI) Foster City, Calif., AUTOMATED MODEL 377® SEQUENCER. The software used for analysis of the resulting data is "SEQUENCE NAVIGATOR® software" purchased through ABI. The BRCA1(omi4) SEQ ID NO:1 sequence is entered into the SEQUENCE NAVIGATOR® software as the Standard for comparison. The SEQUENCE NAVIGATOR® software compares the sample sequence to the BRCA1(omi4) SEQ ID NO:1 standard, base by base. The SEQUENCE NAVIGATOR® software highlights all differences between the BRCA1(omi4) SEQ ID NO:1 DNA sequence and the patient's sample sequence.

A first technologist checks the computerized results by comparing visually the BRCA1(omi4) SEQ ID NO:1 standard against the patient's sample, and again highlights any differences between the standard and the sample. The first primary technologist then interprets the sequence variations at each position along the sequence. Chromatograms from each sequence variation are generated by the SEQUENCE NAVIGATOR® software and printed on a color printer. The peaks are interpreted by the first primary technologist and a second primary technologist. A secondary technologist then reviews the chromatograms. The results are finally interpreted by a geneticist. In each instance, a variation is compared to known polymorphisms for position and base change. Mutations are noted by the length of non-matching variation. Such a lengthy mismatch pattern occurs with deletions and substitutions.

3. Result

Using the above PCR amplification and standard fluorescent sequencing technology, the 3888delGA mutation may be found for example. The 3888delGA mutation of the BRCA1 gene lies in segment "K" segment of exon 11 and will be found in the PCR amplification product for this segment. The DNA sequence results demonstrate the presence of a two base pair deletion at nucleotide position 3888 of the published BRCA1(omi) sequence. This mutation interrupts the reading frame of the BRCA1 transcript, resulting in the appearance of an in-frame terminator (TAG) at codon position 1265. This mutation is, therefore, predicted to result in a truncated, and most likely, non-functional protein. The formal name of the mutation will be 3888delGA. This mutation is named in accordance with the suggested nomenclature for naming mutations, Baudet, et al., *Human Mutation*, 2: 245–248, (1993).

EXAMPLE 4

Generation of Monoclonal and Polyclonal Antibodies Using GST-BRCA1(omi4) Fusion Protein as an Immunogen DNA primers are used to amplify a fragment of BRCA1 (omi4) cDNA (SEQ. ID. NO: 1) using PCR technology. The product is then digested with suitable restriction enzymes and fused in frame with the gene encoding glutathione S-transferase (GST) in *Escherichia coli* using GST expression vector pGEX (Pharmacia Biotech Inc.) The expression of the fusion protein is induced by the addition of isopropyl-β-thiogalactopyranoside. The bacteria are then lysed and the overexpressed fusion protein is purified with glutathione-sepharose beads. The fusion protein is then verified by SDS/PAGE gel and N-terminus protein sequencing. The purified protein is used to immunize rabbits according to standard procedures described in Harlow & Lane (1988). Polycolonal antibody is collected from the serum several weeks after and purified using known methods in the art. Monoclonal antibodies against all or fragments of BRCA1 (omi4) protein, polypeptides, or functional equivalents are obtained using hybridoma technology, see Harlow & Lane (1988). The BRCA1(omi4) protein or polypeptide is coupled to the carrier keyhole limpet hemocyanin in the presence of glutaraldehyde. The conjugated immunogen is mixed with an adjuvant and injected into rabbits. Spleens from antibody-containing rabbits are removed. The B-cells isolated from spleen are fused to myeloma cells using polyethylene glycol (PEG) to promote fusion. The hybrids between the myeloma and B-cells are selected and screened for the production of antibodies to BRCA1(omi4) protein or polypeptide immunogen. Positive cells are recloned to generate monoclonal antibodies.

EXAMPLE 5

Detection of BRCA1 Expression in Human Tissues and Cell Lines

The expression of BRCA1(omi4) in human tissues is determined using Northern blot analysis. Human tissues include those from pancreas, testis, prostate, ovary, breast, small intestine, and colon are obtained from Clontech Laboratories, Inc., Palo Alto, Calif. The poly(A)$^+$ mRNA Northern blots from different human tissues is hybridized to BRCA1(omi4) cDNA probes according to the manufacture protocol. The expression level is further confirmed by RT-PCR using oligo-d(T) as a primer and other suitable primers.

For Northern Blot analysis of cancer cell lines, the human ovarian cancer cell line SKOV-3 and the human breast cancer cell line MCF-7 are obtained from the American Type Culture Collection. Total RNA is prepared by lysing cell in the presence of guanidinium isocyanate. Poly(A)$^+$ mRNA is isolated using the PolyATract mRNA isolation system from Promega, Madison, Wis. The isolated RNA is then electrophoresed under denaturing conditions and transferred to Nylon membrane. The probe used for Northern blot is a fragment of BRCA1(omi4) sequence obtained by PCR amplification. The probes are labeled with [α-$^{32}$P] dCTP using a random-primed labeling kit (Amersham Life Science, Arlington Heights, Ill.).

EXAMPLE 6

Expression of the BRCA1 Protein

The whole-cell extracts of BRCA1(omi4) transfected cells are subjected to immunoprecipitation and immunoblotting to determine the BRCA1 protein level. The BRCA1 protein or polypeptide is immunoprecipitated using anti-BRCA1(omi4) antibodies prepared according to Example 4 or other anti-BRCA1 antibodies purchased from Santa Cruz Biotechnology Inc. Samples are then fractionated using SDS/PAGE gel and transferred to nitrocellulose. Western immunoblotting of the BRCA1 protein is performed with the indicated antibodies. Antibody reaction is revealed using enhanced chemiluminescence reagents (Dupont New England Nuclear, Boston, Mass.).

EXAMPLE 7

Use of the BRCA1(omi4) Gene Therapy

The growth of ovarian or breast cancer may be arrested by increasing the expression of the BRCA1 gene where inadequate expression of that gene is responsible for hereditary ovarian, breast and prostate cancer. It has been demonstrated that transfection of BRCA1 into cancer cells inhibits their growth and reduces tumorigenesis. Gene therapy is performed on a patient to reduce the size of a tumor. The LXSN vector is transformed with the BRCA1(omi4) SEQ ID NO:1 coding region.

Vector

The LXSN vector is transformed with wildtype BRCA1 (omi4) SEQ ID NO:1 coding sequence. The LXSN-BRCA1 (omi4) retroviral expression vector is constructed by cloning a Sal I linkered BRCA1(omi4) cDNA (nucleotides 1–5711) into the Xho I site of the vector LXSN. Constructs are confirmed by DNA sequencing. See Holt et al., *Nature Genetics*, 12: 298–302 (1996). Retroviral vectors are manufactured from viral producer cells using serum free and phenol-red free conditions and tested for sterility, absence of specific pathogens, and absence of replication-competent retrovirus by standard assays. Retrovirus is stored frozen in aliquots which have been tested.

Patients receive a complete physical exam, blood, and urine tests to determine overall health. They may also have a chest X-ray, electrocardiogram, and appropriate radiologic procedures to assess tumor stage.

Patients with metastatic ovarian cancer are treated with retroviral gene therapy by infusion of recombinant LXSN-BRCA1(omi4) retroviral vectors into peritoneal sites containing tumor, between $10^9$ and $10^{10}$ viral particles per dose. Blood samples are drawn each day and tested for the presence of retroviral vector by sensitive polymerase chain reaction (PCR)-based assays. The fluid which is removed is analyzed to determine:

1. The percentage of cancer cells which are taking up the recombinant LXSN-BRCA1(omi4) retroviral vector combination. Successful transfer of BRCA1 gene into cancer cells is shown by both RT-PCR analysis and in situ hybridization. RT-PCR is performed with by the method of Thompson et al., *Nature Genetics*, 9: 444–450 (1995), using primers derived from BRCA1 (omi4) SEQ ID NO:1. Cell lysates are prepared and immunoblotting is performed by the method of Jensen et al., *Nature Genetics*, 12: 303–308 (1996) and Jensen et al., *Biochemistry*, 31: 10887–10892 (1992).
2. Presence of programmed cell death using APOTAG® in situ apoptosis detection kit (ONCOR, INC., Gaithersburg, Md.) and DNA analysis.
3. Measurement of BRCA I gene expression by slide immunofluorescence or Western blot.

Patients with measurable disease are also evaluated for a clinical response to LXSN-BRCAl(omi4), especially those that do not undergo a palliative intervention immediately after retroviral vector therapy. Fluid cytology, abdominal girth, CT scans of the abdomen, and local symptoms are followed.

For other sites of disease, conventional response criteria are used as follows:
1. Complete Response (CR), complete disappearance of all measurable lesions and of all signs and symptoms of disease for at least 4 weeks.

2. Partial Response (PR), decrease of at least 50% of the sum of the products of the 2 largest perpendicular diameters of all measurable lesions as determined by 2 observations not less than 4 weeks apart. To be considered a PR, no new lesions should have appeared during this period and none should have increased in size.
3. Stable Disease, less than 25% change in tumor volume from previous evaluations.
4. Progressive Disease, greater than 25% increase in tumor measurements from prior evaluations. The number of doses depends upon the response to treatment.

For further information related to this gene therpay approach see in "BRCA1 Retroviral Gene Therapy for Ovarian Cancer" a Human Gene Transfer Protocol: NIH ORDA Registration #: 9603-149 Jeffrey Holt, JT, M.D. and Carlos L. Arteaga, M.D.

EXAMPLE 8

Protein Replacement Therapy

Therapeutically elevated level of the functional BRCA1 protein may alleviate the absence or reduced endogenous BRCA1 tumor suppressing activity. Breast or ovarian cancer is treated by the administration of a therapeutically effective amount of BRCA1(omi4) protein, a polypeptide, or its functional equivalent in a pharmaceutically acceptable carrier. Clinically effective delivery method is applied either locally at the site of the tumor or systemically to reach other metastasized locations with known protocols in the art. These protocols may employ the methods of direct injection into a tumor or diffusion using time release capsule. A therapeutically effective dosage is determined by one of skill in the art.

Breast or ovarian cancer may be prevented by the administration of a prophylactically effective amount of the BRCA1(omi4) protein, polypeptide, or its functional equivalent in a pharmaceutically acceptable carrier. Individuals with known risk for breast or ovarian cancer is subjected to protein replacement therapy to prevent tumorigenesis or to decrease the risk of cancer. Elevated risk for breast and ovarian cancer includes factors such as carriers of one or more known BRCA1 and BRCA2 mutations, late child bearing, early onset of menstrual period, late occurrence of menopause, and certain high risk dietary habits. Clinically effective delivery method is used with known protocols in the art, such as administration into peritoneal cavity, or using an implantable time release capsule. A prophylactically effective dosage is determined by one of skill in the art.

Table of References
1. Sanger, et al., *J. Mol. Biol.*, 42: 1617 (1980).
2. Beaucage, et al., *Tetrahedron Letters*, 22: 1859–1862 (1981).
3. Maniatis, et. al., in *Molecular Cloning:A Laboratory Manual,* Cold Spring Harbor, N.Y., p 280–281 (1982).
4. Conner, et. al., *Proc. Natl. Acad. Sci. U.S.A.,* 80: 278 (1983)
5. Saiki, et. al., *Bio/Technology,* 3: 1008–1012 (1985)
6. Landgren, et. al., *Science,* 241: 1007 (1988)
7. Landgren, et. al., *Science,* 242 :229–237 (1988).
8. PCR. A Practical Approach, ILR Press, Eds. M. J. McPherson, P. Quirke, and G. R. Taylor, (1992).
9. Easton et al., *American Journal of Human Genetics,* 52: 678–701 (1993).
10. U.S. Pat. No. 4,458,066.
11. Rowell, et al., *American Journal of Human Genetics,* 55: 861–865 (1994)
12. Miki, et al., *Science,* 266: 66–71 (1994).
13. Friedman, et al., *Nature Genetics,* 8: 399–404 (1994).
14. Baudet, et al., *Human Mutation,* 2: 245–248 (1993).
15. Friend, et al., *Nature Genetics,* 11: 238 (1995).
16. Arteaga and Holt, *Cancer Research,* 56: 1098–1103 (1996).
17. Holt, et al., *Nature Genetics,* 12: 298–302 (1996).
18. Jensen, et al., *Nature Genetics,* 12: 303–308 (1996).
19. Steeg, *Nature Genetics,* 12: 223–225 (1996).
20. Thompson, et al., *Nature Genetics,* 9: 444–450 (1995)
21. Holt and Arteaga, Gene Therapy Protocol ORDA #: 9603-149 ORDA approved Protocol for BRCA1 Gene Therapy.
22. Sambrook, et al., *Molecular Cloning: A Laboratory Manual,* Second Edition, Cold Spring Harbor Laboratory, Cold Spring Harbor, N.Y. (1989).
23. Bertwistle and Ashworth, *Curr. Opin. Genet. Dev.* 8(1): 14–20 (1998).
24. Zhang et al., *Cell* 92:433–436 (1998).
25. Sharan et al., *Nature* 386:804–810 (1997).
26. Katagiri et al., *Genes, Chromosomes & Cancer* 21:217–222 (1988).
27. Crooke, *Annu. Rev. Pharmacol. Toxicol.* 32:329–376 (1992)
28. Robinson-Benion and Holt, *Methods Enzymol.* 254:363–375 (1995).
29. Harlow & Lane, Antibodies: A Laboratory Manual, Cold Spring Harbor Laboratory, Cold Spring Harbor, N.Y., 1988.
30. Shuldiner, et al., *Handbook of Techniques in Endocrine Research,* p. 457–486, DePablo, F., Scanes, C., Eds., Academic Press, Inc., 1993.
31. Holt et al., *Nature Genetics* 12: 298–302 (1996).
32. Thompson et al., *Nature Genetics* 9: 444–450 (1995).
33. Jensen et al., *Nature Genetics* 12: 303–308 (1996)
34. Jensen et al., *Biochemistry* 31: 10887–10892 (1992).
35. U.S. Pat. No. 5,593,840
36. U.S. Pat. No. 5,445,934
37. U.S. Pat. No. 5,510,270
38. U.S. Pat. No. 5,547,839
39. Kenneth W. Culver, in Gene Therapy A Primer For Physicians, 2d Ed. Mary Ann Liebert Inc. (1996).
40. U.S. Pat. No. 5,583,013.
41. Husain et al., *Cancer Res.* 58:1120–1123 (1998).
42. Ruffner et al., *Proc. Natl. Acad. Sci. USA* 94:7138–7143 (1997)
43. Shattuck-Eidens et al., *J. Am. Med. Assn.* 278(15) 1242–1250 (1997)
44. U.S. Pat. No. 5,650,316
45. U.S. Pat. No. 5,624,803
46. U.S. Pat. No. 5,654,155

Claims in this document which recite breast and/or ovarian cancer refer to breast, ovarian, prostate and colon cancers in men and women.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are within the scope of the appended claims. Accordingly, the invention is limited only by the following claims.

All references mentioned herein are incorporated by reference.

We claim:

1. An isolated nucleic acid molecule that encodes a BRCA1 protein comprising a first nucleotide substitution of adenine for guanine at a position corresponding to nucleotide 3232 of SEQ ID NO: 1, and a second nucleotide substitution of cytosine for thymine at a position corresponding to nucleotide 4427 of SEQ ID NO: 1, and fragments thereof containing the first and second nucleotide substitutions.

2. The isolated nucleic acid molecule of claim 1, wherein the nucleic acid molecule encoding the BRCA1 protein further comprises one or more additional nucleotide substitutions selected from the group consisting of:

(a) a cytosine for thymine substitution at a position corresponding to nucleotide 2201 of SEQ ID NO: 1, (b) a thymine for guanine substitution at a position corresponding to nucleotide 2430 of SEQ ID NO: 1, (c) a thymine for cytosine substitution at a position corresponding to nucleotide 2731 of SEQ ID NO: 1, (d) a guanine for adenine substitution at a position corresponding to nucleotide 3667 of SEQ ID NO: 1, and (e) a guanine for adenine substitution at a position corresponding to nucleotide 4956 of SEQ ID NO: 1.

3. The isolated nucleic acid molecule of claim 1, wherein the fragment thereof containing the first and second nucleotide substitutions further comprises one or more substitutions selected from the group consisting of:

(a) a cytosine for thymine substitution at a position corresponding to nucleotide 2201 of SEQ ID NO: 1, (b) a thymine for guanine substitution at a position corresponding to nucleotide 2430 of SEQ ID NO: 1, (c) a thymine for cytosine substitution at a position corresponding to nucleotide 2731 of SEQ ID NO: 1, (d) a guanine for adenine substitution at a position corresponding to nucleotide 3667 of SEQ ID NO: 1, and (e) a guanine for adenine substitution at a position corresponding to nucleotide 4956 of SEQ ID NO: 1.

4. The isolated nucleic acid molecule of claim 1, wherein the nucleic acid comprises the nucleotide sequence of SEQ ID NO: 1.

5. The isolated nucleic acid molecule of claim 4, wherein the nucleic acid molecule consists of the nucleotide sequence of SEQ ID NO: 1.

6. The isolated nucleic acid molecule of claim 1, wherein the nucleic acid molecule comprises nucleotides 120 to 5,708 of SEQ ID NO: 1.

7. The isolated nucleic acid molecule of claim 6, wherein the nucleic acid molecule consists of nucleotides 120 to 5,708 of SEQ ID NO: 1.

8. The isolated nucleic acid molecule of claim 1, wherein the nucleic acid molecule encodes a BRCA1 protein with a glutamate residue at a position corresponding to amino acid 1038 of SEQ ID NO: 2.

9. An isolated nucleic acid molecule that encodes a BRCA1 protein containing a glutamate residue at a position corresponding to amino acid 1038 of SEQ ID NO: 2 and a serine residue at a position corresponding to amino acid 1436 of SEQ ID NO: 1.

10. The isolated nucleic acid molecule of claim 8 or 9, wherein the nucleic acid molecule encodes a BRCA1 protein comprising SEQ ID NO: 2.

11. The isolated nucleic acid molecule of claim 8 or 9, wherein the nucleic acid molecule encodes a BRCA1 protein consisting of SEQ ID NO: 2.

12. The isolated nucleic acid molecule of claim 9, wherein the nucleic acid molecule contains a adenine at a position corresponding to nucleotide 3232 of SEQ ID NO: 1 and a cytosine at a position corresponding to nucleotide 4427 of SEQ ID NO: 1.

13. The isolated nucleic acid molecule of claim 9, wherein the nucleic acid molecule comprises SEQ ID NO: 1.

14. The isolated nucleic acid molecule of claim 13, wherein the nucleic acid molecule consists of SEQ ID NO: 1.

15. The isolated nucleic acid molecule of claim 9, wherein the nucleic acid molecule comprises nucleotides 120 to 5,708 of SEQ ID NO: 1.

16. The isolated nucleic acid molecule of claim 15, wherein the nucleic acid molecule consists of nucleotides 120 to 5,708 of SEQ ID NO: 1.

17. The isolated nucleic acid molecule of claim 1 or 9, wherein said nucleic acid molecule is operably linked to one or more expression control elements.

18. A vector comprising an isolated nucleic acid molecule of claim 1 or 9.

19. A host cell comprising the vector of claim 18.

20. A host cell transformed to contain the nucleic acid molecule of claim 1 or 9.

21. A host cell of claim 20, wherein said host is selected from the group consisting of prokaryotic hosts and eukaryotic hosts.

22. A method for producing a polypeptide comprising culturing a host cell of claim 20 under conditions in which the protein encoded by the nucleic acid molecule is expressed.

23. The method of claim 22, wherein said host cell is selected from the group consisting of prokaryotic hosts and eukaryotic hosts.

24. A nucleic acid molecule of about 10 to about 100 nucleotides which specifically hybridizes to a nucleic acid molecule encoding a BRCA1 protein that contains an adenine for guanine substitution at a position corresponding to nucleotide 3232 of SEQ ID NO: 1.

25. A nucleic acid molecule of about 10 to about 100 nucleotides which specifically hybridizes to a nucleic acid molecule encoding a BRCA1 protein that contains a cytosine for thymine substitution at a position corresponding to nucleotide 4427 of SEQ ID NO: 1.

* * * * *